United States Patent
Foley et al.

(10) Patent No.: US 9,138,596 B2
(45) Date of Patent: Sep. 22, 2015

(54) OPTICAL DEPOLARIZATION OF CARDIAC TISSUE

(75) Inventors: John Foley, Lino Lakes, MN (US); Craig Stolen, New Brighton, MN (US); Mark Schwartz, White Bear Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1337 days.

(21) Appl. No.: 11/895,022

(22) Filed: Aug. 22, 2007

(65) Prior Publication Data

US 2009/0054954 A1 Feb. 26, 2009

(51) Int. Cl.
 *A61N 5/06* (2006.01)
 *A61B 5/04* (2006.01)
 *A61B 5/00* (2006.01)

(52) U.S. Cl.
 CPC ............ *A61N 5/0622* (2013.01); *A61N 5/0601* (2013.01); *A61N 5/062* (2013.01); *A61B 5/04012* (2013.01); *A61B 5/418* (2013.01); *A61N 2005/063* (2013.01); *A61N 2005/0651* (2013.01)

(58) Field of Classification Search
 CPC .............................. A61N 5/06–5/0625; A61N 2005/06–2005/067; A61N 1/36–1/3993
 See application file for complete search history.

(56) References Cited

U.S. PATENT DOCUMENTS

| | | | |
|---|---|---|---|
| 4,051,842 A | 10/1977 | Hazel et al. | |
| 4,140,122 A | 2/1979 | Kuhl et al. | |
| 4,383,529 A | 5/1983 | Webster | |
| 5,111,832 A * | 5/1992 | Saksena | 128/898 |
| 5,383,910 A * | 1/1995 | den Dulk | 607/14 |
| 6,708,058 B2 | 3/2004 | Kim et al. | |
| 2003/0040080 A1 | 2/2003 | Miesenbock et al. | |
| 2005/0202398 A1 | 9/2005 | Hegemann et al. | |
| 2006/0155348 A1* | 7/2006 | deCharms | 607/89 |
| 2007/0060984 A1 | 3/2007 | Webb et al. | |
| 2007/0244524 A1* | 10/2007 | Qu et al. | 607/88 |
| 2008/0200769 A1* | 8/2008 | Sharma et al. | 600/300 |

FOREIGN PATENT DOCUMENTS

| | | |
|---|---|---|
| WO | WO-00/13747 A1 | 3/2000 |
| WO | WO-2006/055582 A2 | 5/2006 |
| WO | WO-2009/025819 A1 | 2/2009 |

OTHER PUBLICATIONS

"International Application Serial No. PCT/US2008/009908, International Search Report mailed Jan. 14, 2009", 6 pgs.

"International Application Serial No. PCT/US2008/009908, Written Opinion mailed Jan. 14, 2009", 9 pgs.

Banghart, M., et al., "Light-activated ion channels for remote control of neuronal firing", *Nat Neurosci.*, 7(12), (2004), 1381-1386.

Li, X., et al., "Fast noninvasive activation and inhibition of neural and network activity by vertebrate rhodopsin and green algae channelrhodopsin", *Proc Natl Acad Sci USA*, 102(49), (2005), 17816-17821.

(Continued)

*Primary Examiner* — Lynsey Crandall

(74) *Attorney, Agent, or Firm* — Schwegman Lundberg & Woessner, P.A.

(57) ABSTRACT

The invention provides a cardiac rhythm management system for stimulating a heart having photosensitive tissue, vectors useful to photosensitize cells expressing the vectors, and methods for light induced depolarization of cells.

15 Claims, 15 Drawing Sheets

(1 of 15 Drawing Sheet(s) Filed in Color)

(56) References Cited

OTHER PUBLICATIONS

Melyan, Z., et al., "Addition of human melanopsin renders mammalian cells photoresponsive", *Nature*, 433(7027), (Feb. 17, 2005), 741-745.

Palczewski, K., et al., "Crystal structure of rhodopsin: A G protein-coupled receptor", *Science*, 289(5480), (Aug. 4, 2000), 739-45.

Panda, S., et al., "Illumination of the melanopsin signaling pathway", *Science*, 307(5709), (Jan. 28, 2005), 600-604.

Qiu, X., et al., "Induction of photosensitivity by heterologous expression of melanopsin", *Nature*, 433(7027), (2005), 745-749.

Yokoyama, S., et al., "The spectral tuning in the short wavelength-sensitive type 2 pigments", *Gene*, 306, (2003), 91-98.

\* cited by examiner

```
BR  ion channel - 568 nm λ max
ChR2 ion channel - 500 nm λ max

BR    91   IYWARYADWLFTTPLLLLDLALIVDADQGTILALVGADGIMIGTGLVGALTKVYSYRFVW
                + W  RYA+WL  T P++L+ L+    +G     IGT                  VW
ChR2  116  VQWLRYAEWLLTCPVLLIHLSNLTGLSNDYSRRTMGLLVSDIGT------------IVW

BR    151  WSAISTAAMLYILYVLF------FGFTSKAESMRPEVASTFKVLRNVT------VVL
                A S A  Y+ + F        F   +KA             +  VI       V
ChR2  163  GATSAMATGYVKVIFFCLGLCYGANTFFHAAKAYIEGYHTVPKGRCRQVVTGMAWLFFVS

BR    195  WSAYFVVLIGSEGAGIVPLNIETLLFMVLDVSAKVGFGLI                    235
            W +F+++++G EG G++  +      T+    ++D+   +K  +GL+
ChR2  223  WGMFPILFILGPEGFGVLSVYGSTVGHTIIDLMSKNCWGLL                    263
```

FIG. 5

```
  1  mdyggalsav  grellfvtnp  vvvngsvlvp  edqcycagwi  esrgtngaqt  asnvlqwlaa
 61  gfsilllmfy  ayqtwkstcg  weeiyvcaie  mvkvilefff  efknpsmlyl  atghrvqwlr
121  yaewlltcpv  ilihlsnltg  lsndysrrtm  gllvsdigti  vwgatsamat  gyvkviffcl
181  glcygantff  haakayiegy  htvpkgrcrq  vvtgmawlff  vswgmfpilf  ilgpegfgvl
241  svygstvght  iidlmskncw  gllghylrvl  ihehilihgd  irkttklnig  gteievetlv
301  edeaeagavn  kgtgkyasre  sflvmrdkmk  ekgidvrasl  dnskeveqeq  aaraammmmn
361  gngmgmgmgm  ngmngmggmn  gmaggakpgl  eltpqlqpgr  vilavpdism  vdffreqfaq
421  lsvtyelvpa  lgadntlalv  tqaqnlggvd  fvlihpeflr  drsstsilsr  lrgagqrvaa
481  fgwaqlgpmr  dliesanldg  wlegpsfgqg  ilpahivalv  akmqqmrkmq  qmqqigmmtg
541  gmngmgggmg  ggmngmgggn  gmnnmgngmg  ggmgngmggn  gmngmgggng  mnnmggngma
601  gngmgggmgg  ngmggsmngm  ssgvvanvtp  saaggmggmm  nggmaapqsp  gmnggrlgtn
661  plfnaapspl  ssqlgaeagm  gsmggmggms  gmggmggmgg  mggagaattq  aaggnaeaem
721  lqnlmneinr  lkrelge
```

FIG. 6A

```
   1  gcatctgtcg  ccaagcaagc  attaaacatg  gattatggag  gcgccctgag  tgccgttggg
  61  cgcgagctgc  tatttgtaac  gaacccagta  gtcgtcaatg  gctctgtact  tgtgcctgag
 121  gaccagtgtt  actgcgcggg  ctggattgag  tcgcgtggca  caaacggtgc  ccaaacggcg
 181  tcgaacgtgc  tgcaatggct  tgctgctggc  ttctccatcc  tactgcttat  gttttacgcc
 241  taccaaacat  ggaagtcaac  ctgcggctgg  gaggagatct  atgtgtgcgc  tatcgagatg
 301  gtcaaggtga  ttctcgagtt  cttcttcgag  tttaagaacc  cgtccatgct  gtatctagcc
 361  acaggccacc  gcgtccagtg  gttgcgttac  gccgagtggc  ttctcacctg  cccggtcatt
 421  ctcattcacc  tgtcaaacct  gacgggcttg  tccaacgact  acagcaggcg  caccatgggt
 481  ctgcttgtgt  ctgatattgg  cacaattgtg  tggggcgcca  cttccgccat  ggccaccgga
 541  tacgtcaagg  tcatcttctt  ctgcctgggt  ctgtgttatg  gtgctaacac  gttctttcac
 601  gctgccaagg  cctacatcga  gggttaccac  accgtgccga  agggccggtg  tcgccaggtg
 661  gtgactggca  tggcttggct  cttcttcgta  tcatggggta  tgttccccat  cctgttcatc
 721  ctcggccccg  agggcttcgg  cgtcctgagc  gtgtacggct  ccaccgtcgg  ccacaccatc
 781  attgacctga  tgtcgaagaa  ctgctcgggt  ctgctcggcc  actacctgcg  cgtgctgatc
 841  cacgagcata  tcctcatcca  cggcgacatt  cgcaagacca  ccaaattgaa  cattggtggc
 901  actgagattg  aggtcgagac  gctggtggag  gacgaggccg  aggctggcgc  ggtcaacaag
 961  ggcaccggca  agtacgcctc  ccgcgagtcc  ttcctggtca  tgcgcgacaa  gatgaaggag
1021  aagggcattg  acgtgcgcgc  ctctctggac  aacagcaagg  aggtggagca  ggagcaggcc
1081  gccaggctg   ccatgatgat  gatgaacggc  aatggcatgg  gtatgggaat  gggaatgaac
1141  ggcatgaacg  gaatgggcgg  tatgaacggg  atggctggcg  gcgccaagcc  cggcctggag
1201  ctcactccgc  agctacagcc  cggccgcgtc  atcctggcgg  tgccggacat  cagcatggtt
1261  gacttcttcc  gcgagcagtt  tgctcagcta  tcggtgacgt  acgagctggt  gccggccctg
1321  ggcgctgaca  acacactggc  gctggttacg  caggcgcaga  acctgggcgg  cgtggacttt
1381  gtgttgattc  accccgagtt  cctgcgcgac  cgctctagca  ccagcatcct  gagccgcctg
1441  cgcggcgcgg  gccagcgtgt  ggctgcgttc  ggctgggcgc  agctggggcc  catgcgtgac
1501  ctgatcgagt  ccgcaaacct  ggacggctgg  ctggagggcc  cctcgttcgg  acagggcatc
1561  ctgccggccc  acatcgttgc  cctggtggcc  aagatgcaga  agatgcgcaa  gatgcagcag
1621  atgcagcaga  ttggcatgat  gaccggcggc  atgaacggca  tgggcggcgg  tatgggcggc
1681  ggcatgaacg  gcatgggcgg  cggcaacggc  atgaacaaca  tgggcaacgg  catgggcggc
1741  ggcatgggca  acggcatggg  cggcaatggc  atgaacggaa  tgggtggcgg  caacggcatg
1801  aacaacatgg  gcggcaacgg  aatggccggc  aacgaatggg  gcggcggcat  gggcggcaac
1861  ggtatgggtg  gctccatgaa  cggcatgagc  tccggcgtgg  tggccaacgt  gacgccctcc
1921  gccgccggcg  gcatgggcgg  catgatgaac  ggcggcatgg  ctgcgcccca  gtcgcccggc
1981  atgaacggcg  gccgcctggg  taccaacccg  ctcttcaacg  ccgcgccctc  accgctcagc
2041  tcgcagctcg  gtgccgaggc  aggcatggag  agcatgggag  gcatgggagg  aatgagcgga
2101  atgggaggca  tgggtggaat  gggggggcatg  ggcggcgccg  gcgccgccac  gacgcaggct
2161  gcgggcggca  acgcggaggc  ggagatgctg  cagaatctca  tgaacgagat  caatcgcctg
2221  aagcgcgagc  ttggcgagta  a
```

FIG. 6B

|   |   |   |   |   |   |   |
|---|---|---|---|---|---|---|
| 1 | msrrpwllal | alavalaags | agastgsdat | vpvatqdgpd | yvfhraherm | lfqtsytlen |
| 61 | ngsvicipnn | gqcfclawlk | sngtnaekla | anilqwitfa | lsalclmfyg | yqtwkstcgw |
| 121 | eeiyvatiem | ikfiieyfhe | fdepaviyss | ngnktvwlry | aewlltcpvi | lihlsnltgl |
| 181 | andynkrtmg | llvsdigtiv | wgttaalskg | yvrvifflmg | lcygiytffn | aakvyieayh |
| 241 | tvpkgicrdl | vrylawlyfc | swamfpvlfl | lgpegfghin | qfnsaiahai | ldlasknaws |
| 301 | mmghflrvki | hehillygdi | rkkqkvnvag | qemevetmvh | eeddetqkvp | takyanrdsf |
| 361 | iimrdrlkek | gfetrasldg | dpngdaeana | aaggkpgmem | gkmtgmgmgm | gagmgmatid |
| 421 | sgrvilavpd | ismvdffreq | farlpvpyel | vpalgaentl | qlvqqaqslg | gcdfvlmhpe |
| 481 | flrdrsptgl | lprlkmggqr | aaafgwaaig | pmrdliegsg | vdgwlegpsf | gaginqqalv |
| 541 | alinrmqqak | kmgmmggmgm | gmgggmgmgm | gmgmgmapsm | nagmtggmgg | asmggavmgm |
| 601 | gmgmqpmqqa | mpamspmmtq | qpsmmsqpsa | msaggamqam | ggvmpspapg | grvgtnplfg |
| 661 | sapsplssqp | gispgmatpp | aataapaagg | seaemlqqlm | seinrlknel | ge |

*FIG. 6C*

|   |   |   |   |   |   |   |
|---|---|---|---|---|---|---|
| 1 | gcgttgcttg | actacgcttc | gctgtaataa | tagcagcgcc | acaagtagtg | tcgccaaaca |
| 61 | actctcactt | tgagcttgag | cacaccgctg | agcccgatg | tcgcggaggc | catggcttct |
| 121 | tgccctagcg | ctggcagtgg | cgctggcggc | cggcagcgca | ggagcctcga | ctggcagtga |
| 181 | cgcgacggtg | ccggtcgcga | ctcaggatgg | ccccgactac | gttttccacc | gtgcccacga |
| 241 | gcgcatgctc | ttccaaacct | catacactct | tgagaacaat | ggttctgtta | tttgcatccc |
| 301 | gaacaacggc | cagtgcttct | gcttggcttg | gcttaaatcc | aacggaacaa | atgccgagaa |
| 361 | gttggctgcc | aacattctgc | agtggattac | ttttgcgctt | tcagcgctct | gcctgatgtt |
| 421 | ctacggctac | cagacctgga | agtctacttg | cggctgggag | gagatttacg | tggccacgat |
| 481 | cgagatgatc | aagttcatca | tcgagtattt | ccatgagttt | gacgaacctg | cggtgatcta |
| 541 | ctcatccaac | ggcaacaaga | ccgtgtggct | tcgttacgcg | gagtggctgc | tgacctgccc |
| 601 | tgtcattctt | atccatctga | gcaaccttac | gggtctggcg | aacgactata | acaagcgtac |
| 661 | catgggtctg | ctggtgtcag | atatcggcac | gatcgtgtgg | ggcaccacgg | ccgcgctgtc |
| 721 | caaggatac | gtccgtgtca | ttttcttcct | gatgggcctg | tgctacggca | tctacacatt |
| 781 | cttcaacgca | gccaaggtct | acattgaggc | gtaccacacc | gtgcccaagg | gcatttgccg |
| 841 | cgacctggtc | cgctaccttg | cctggctcta | cttctgttca | tgggctatgt | tcccggtgct |
| 901 | gttcctgctg | ggccccgagg | gctttggcca | catcaaccaa | ttcaactctg | ccatcgccca |
| 961 | cgccatcctg | gaccttgcct | ccaagaacgc | ttggagtatg | atgggtcact | ttctgcgtgt |
| 1021 | caagatccac | gagcacatcc | tgctgtacgg | cgacatccgc | aagaagcaga | aggtcaacgt |
| 1081 | ggctggccag | gagatggagg | tggagaccat | ggtgcacgag | gaggacgacg | agacgcagaa |
| 1141 | ggtgcccacg | gcaaagtacg | ccaaccgcga | ctcgttcatc | atcatgcgcg | accgcctcaa |
| 1201 | ggagaagggc | ttcgagaccc | gcgcctcgct | ggacggcgac | ccgaacggcg | acgccgaggc |
| 1261 | caacgctgca | gccggcggca | agcccggaat | ggagatgggc | aagatgaccg | gcatgggcat |
| 1321 | gggcatgggt | gccggcatgg | gcatggcgac | catcgattcg | ggccgcgtca | tcctcgccgt |
| 1381 | gccggacatc | tccatggtgg | acttttccg | cgagcagttc | gcgcggctgc | ccgtgcccta |
| 1441 | cgaactggtg | cccgcgctgg | gcgcggagaa | caccctccag | ctggtgcagc | aggcgcagtc |
| 1501 | actgggaggc | tgcgacttcg | tcctcatgca | ccccgagttc | ctgcgcgacc | gcagtcccac |
| 1561 | gggtctgctg | ccccgcctca | agatgggcgg | gcagcgcgcc | gcggccttcg | gctgggcggc |
| 1621 | aatcggcccc | atgcgggact | tgatcgaggg | ttcgggcgtt | gacggctggc | tggagggccc |
| 1681 | cagctttggc | gccggcatca | accagcaggc | gctggtggcg | ctgatcaacc | gcatgcagca |
| 1741 | ggccaagaag | atgggcatga | tggcggtat | gggtatgggc | atgggcggcg | gcatgggtat |
| 1801 | gggcatgggt | atgggcatgg | gcatggcccc | cagcatgaac | gccggcatga | ctggcggcat |
| 1861 | gggcggcgcc | tccatgggcg | gtgccgtgat | gggcatgggc | atggcgatgc | agcccatgca |
| 1921 | gcaggctatg | ccggccatgt | cgcccatgat | cgcccatgca | ggccatgggt | ggcgtcatgc |
| 1981 | ctccgccatg | agcgccggcg | gcgccatgca | ggccatgggt | ggcgtcatgc | ccagccccgc |
| 2041 | ccccggcggc | cgcgtgggca | ccaacccgct | gtttggctct | gcgccctctc | cgctgagctc |
| 2101 | gcagcccggc | atcagccctg | gcatggcgac | gccgcccgcc | gccaccgccg | cacccgccgc |
| 2161 | tggcggcagc | gaggccgaga | tgctgcagca | gctgatgagc | gagatcaacc | gcctgaagaa |
| 2221 | cgagctgggc | gagtaa |   |   |   |   |

*FIG. 6D*

```
  1  mlellptave  gvsqaqitgr  pewiwlalgt  almlgtlyf   lvkgmgvsdp  dakkfyaitt
 61  lvpaiaftmy  lsmllgyglt  mvpfggeqnp  iywaryadwl  fttplllldl  allvdadggt
121  ilalvgadgi  migtglvgal  tkvysyrfvw  waistaamly  ilyvlffgft  skaesmrpev
181  astfkvlrnv  tvvlwsaypv  vwligsegag  ivplnietll  fmvldvsakv  gfglillrer
241  aifgeaeape  psagdgaaat  sd
```

FIG. 6E

SEQUENCE LISTING

```
<160> NUMBER OF SEQ ID NOS: 7

<210> SEQ ID NO 1
<211> LENGTH: 737
<212> TYPE: PRT
<213> ORGANISM: C. reinhardtii

<400> SEQUENCE: 1

Met Asp Tyr Gly Gly Ala Leu Ser Ala Val Gly Arg Glu Leu Leu Phe
 1               5                  10                  15

Val Thr Asn Pro Val Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
```

-continued

```
                50                  55                  60
Leu Leu Leu Met Phe Tyr Ala Tyr Gln Thr Trp Lys Ser Thr Cys Gly
 65                  70                  75                  80

Trp Glu Glu Ile Tyr Val Cys Ala Ile Glu Met Val Lys Val Ile Leu
                     85                  90                  95

Glu Phe Phe Phe Glu Phe Lys Asn Pro Ser Met Leu Tyr Leu Ala Thr
                    100                 105                 110

Gly His Arg Val Gln Trp Leu Arg Tyr Ala Glu Trp Leu Leu Thr Cys
                115                 120                 125

Pro Val Ile Leu Ile His Leu Ser Asn Leu Thr Gly Leu Ser Asn Asp
                130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
                180                 185                 190

Ala Lys Ala Tyr Ile Glu Gly Tyr His Thr Val Pro Lys Gly Arg Cys
                195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                    245                 250                 255

Lys Asn Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
                275                 280                 285

Ile Gly Gly Thr Glu Ile Glu Val Glu Thr Leu Val Glu Asp Glu Ala
290                 295                 300

Glu Ala Gly Ala Val Asn Lys Gly Thr Gly Lys Tyr Ala Ser Arg Glu
305                 310                 315                 320

Ser Phe Leu Val Met Arg Asp Lys Met Lys Glu Lys Gly Ile Asp Val
                    325                 330                 335

Arg Ala Ser Leu Asp Asn Ser Lys Glu Val Glu Gln Glu Gln Ala Ala
                340                 345                 350

Arg Ala Ala Met Met Met Met Asn Gly Asn Gly Met Gly Met Gly Met
                355                 360                 365

Gly Met Asn Gly Met Asn Gly Met Gly Gly Met Asn Gly Met Ala Gly
                370                 375                 380

Gly Ala Lys Pro Gly Leu Glu Leu Thr Pro Gln Leu Gln Pro Gly Arg
385                 390                 395                 400

Val Ile Leu Ala Val Pro Asp Ile Ser Met Val Asp Phe Phe Arg Glu
                    405                 410                 415

Gln Phe Ala Gln Leu Ser Val Thr Tyr Glu Leu Val Pro Ala Leu Gly
                420                 425                 430

Ala Asp Asn Thr Leu Ala Leu Val Thr Gln Ala Gln Asn Leu Gly Gly
                435                 440                 445

Val Asp Phe Val Leu Ile His Pro Glu Phe Leu Arg Asp Arg Ser Ser
                450                 455                 460

Thr Ser Ile Leu Ser Arg Leu Arg Gly Ala Gly Gln Arg Val Ala Ala
465                 470                 475                 480
```

Phe Gly Trp Ala Gln Leu Gly Pro Met Arg Asp Leu Ile Glu Ser Ala
              485                 490                 495

Asn Leu Asp Gly Trp Leu Glu Gly Pro Ser Phe Gly Gln Gly Ile Leu
          500                 505                 510

Pro Ala His Ile Val Ala Leu Val Ala Lys Met Gln Gln Met Arg Lys
      515                 520                 525

Met Gln Gln Met Gln Gln Ile Gly Met Met Thr Gly Gly Met Asn Gly
  530                 535                 540

Met Gly Gly Gly Met Gly Gly Met Asn Gly Met Gly Gly Asn
545                 550                 555                 560

Gly Met Asn Asn Met Gly Asn Gly Met Gly Gly Met Gly Asn Gly
              565                 570                 575

Met Gly Gly Asn Gly Met Asn Gly Met Gly Gly Asn Gly Met Asn
          580                 585                 590

Asn Met Gly Gly Asn Gly Met Ala Gly Asn Gly Met Gly Gly Met
      595                 600                 605

Gly Gly Asn Gly Met Gly Gly Ser Met Asn Gly Met Ser Ser Gly Val
          610                 615                 620

Val Ala Asn Val Thr Pro Ser Ala Ala Gly Met Gly Gly Met Met
625                 630                 635                 640

Asn Gly Gly Met Ala Ala Pro Gln Ser Pro Gly Met Asn Gly Gly Arg
              645                 650                 655

Leu Gly Thr Asn Pro Leu Phe Asn Ala Ala Pro Ser Pro Leu Ser Ser
          660                 665                 670

Gln Leu Gly Ala Glu Ala Gly Met Gly Ser Met Gly Gly Met Gly Gly
      675                 680                 685

Met Ser Gly Met Gly Gly Met Gly Gly Met Gly Gly Met Gly Gly Ala
  690                 695                 700

Gly Ala Ala Thr Thr Gln Ala Ala Gly Gly Asn Ala Glu Ala Glu Met
705                 710                 715                 720

Leu Gln Asn Leu Met Asn Glu Ile Asn Arg Leu Lys Arg Glu Leu Gly
              725                 730                 735

Glu

<210> SEQ ID NO 2
<211> LENGTH: 2241
<212> TYPE: DNA
<213> ORGANISM: C. reinhardtii

<400> SEQUENCE: 2
gcatctgtcg ccaagcaagc attaaacatg gattatggag gcgccctgag tgccgttggg      60
cgcgagctgc tatttgtaac gaacccagta gtcgtcaatg gctctgtact tgtgcctgag     120
gaccagtgtt actgcgcggg ctggattgag tcgcgtggca caaacggtgc ccaaacggcg     180
tcgaacgtgc tgcaatggct tgctgctggc ttctccatcc tactgcttat gttttacgcc     240
taccaaacat ggaagtcaac ctgcggctgg gaggagatct atgtgtgcgc tatcgagatg     300
gtcaaggtga ttctcgagtt cttcttcgag tttaagaacc cgtccatgct gtatctagcc     360
acaggccacc gcgtccagtg gttgcgttac gccgagtggc ttctcacctg cccggtcatt     420
ctcattcacc tgtcaaacct gacgggcttg tccaacgact acagcaggcg caccatgggt     480
ctgcttgtgt ctgatattgg cacaattgtg tggggcgcca cttccgccat ggccaccgga     540
tacgtcaagg tcatcttctt ctgcctgggt ctgtgttatg tgctaacac gttctttcac     600

```
gctgccaagg cctacatcga gggttaccac accgtgccga agggccggtg tcgccaggtg    660
gtgactggca tggcttggct cttcttcgta tcatggggta tgttccccat cctgttcatc    720
ctcggccccg agggcttcgg cgtcctgagc gtgtacggct ccaccgtcgg ccacaccatc    780
attgacctga tgtcgaagaa ctgctggggt ctgctcggcc actacctgcg cgtgctgatc    840
cacgagcata tcctcatcca cggcgacatt cgcaagacca ccaaattgaa cattggtggc    900
actgagattg aggtcgagac gctggtggag gacgaggccg aggctggcgc ggtcaacaag    960
ggcaccggca agtacgcctc ccgcgagtcc ttcctggtca tgcgcgacaa gatgaaggag   1020
aagggcattg acgtgcgcgc ctctctggac aacagcaagg aggtggagca ggagcaggcc   1080
gccagggctg ccatgatgat gatgaacggc aatggcatgg gtatgggaat gggaatgaac   1140
ggcatgaacg gaatgggcgg tatgaacggg atggctggcg cgccaagcc cggcctggag    1200 ctcactccgc agctacagcc cggccgcgtc atcctggcgg tgccggacat cagcatggtt   1260
gacttcttcc gcgagcagtt tgctcagcta tcggtgacgt acgagctggt gccggccctg   1320
ggcgctgaca acacactggc gctggttacg caggcgcaga acctgggcgg cgtggacttt   1380
gtgttgattc accccgagtt cctgcgcgac cgctctagca ccagcatcct gagccgcctg   1440
cgcggcgcgg ccagcgtgt ggctgcgttc ggctgggcgc agctgggcgc catgcgtgac    1500
ctgatcgagt ccgcaaacct ggacggctgg ctggagggcc cctcgttcgg acagggcatc   1560
ctgccggccc acatcgttgc cctggtggcc aagatgcagc agatgcgcaa gatgcagcag   1620
atgcagcaga ttggcatgat gaccggcggc atgaacggca tgggcggcgg tatgggcggc   1680
ggcatgaacg gcatgggcgg cggcaacggc atgaacaaca tgggcaacgg catgggcggc   1740
ggcatgggca acggcatggg cggcaatggc atgaacggaa tgggtggcgg caacggcatg   1800
aacaacatgg gcgcaacgg aatggccggc aacggaatgg gcggcggcat gggcggcaac    1860
ggtatgggtg gctccatgaa cggcatgagc tccggcgtgg tggccaacgt gacgccctcc   1920
gccgccggcg gcatgggcgg catgatgaac ggcggcatgg ctgcgcccca gtcgcccggc   1980
atgaacggcg gccgcctggg taccaacccg ctcttcaacg ccgcgccctc accgctcagc   2040
tcgcagctcg gtgccgaggc aggcatgggc agcatgggag gcatgggcgg aatgagcgga   2100
atgggaggca tgggtggaat gggggggcatg ggcggcgccg cgccgccac gacgcaggct   2160 gcgggcggca acgcggaggc ggagatgctg cagaatctca tgaacgagat caatcgcctg   2220
aagcgcgagc ttggcgagta a                                              2241
```

<210> SEQ ID NO 3
<211> LENGTH: 712
<212> TYPE: PRT
<213> ORGANISM: C. reinhardtii

<400> SEQUENCE: 3

```
Met Ser Arg Arg Pro Trp Leu Leu Ala Leu Ala Leu Ala Val Ala Leu
 1               5                  10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80
```

-continued

```
Ser Asn Gly Thr Asn Ala Glu Lys Leu Ala Asn Ile Leu Gln Trp
                 85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
            115                 120                 125

Glu Met Ile Lys Phe Ile Ile Glu Tyr Phe His Glu Phe Asp Glu Pro
130             135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Ile Leu Ile His Leu Ser Asn
                165                 170                 175

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Thr Ala Ala Leu Ser
            195                 200                 205

Lys Gly Tyr Val Arg Val Ile Phe Phe Leu Met Gly Leu Cys Tyr Gly
            210                 215                 220

Ile Tyr Thr Phe Phe Asn Ala Ala Lys Val Tyr Ile Glu Ala Tyr His
225                 230                 235                 240

Thr Val Pro Lys Gly Ile Cys Arg Asp Leu Val Arg Tyr Leu Ala Trp
                245                 250                 255

Leu Tyr Phe Cys Ser Trp Ala Met Phe Pro Val Leu Phe Leu Leu Gly
                260                 265                 270

Pro Glu Gly Phe Gly His Ile Asn Gln Phe Asn Ser Ala Ile Ala His
                275                 280                 285

Ala Ile Leu Asp Leu Ala Ser Lys Asn Ala Trp Ser Met Met Gly His
290                 295                 300

Phe Leu Arg Val Lys Ile His Glu His Ile Leu Leu Tyr Gly Asp Ile
305                 310                 315                 320

Arg Lys Lys Gln Lys Val Asn Val Ala Gly Gln Glu Met Glu Val Glu
                325                 330                 335

Thr Met Val His Glu Glu Asp Glu Thr Gln Lys Val Pro Thr Ala
            340                 345                 350

Lys Tyr Ala Asn Arg Asp Ser Phe Ile Ile Met Arg Asp Arg Leu Lys
                355                 360                 365

Glu Lys Gly Phe Glu Thr Arg Ala Ser Leu Asp Gly Asp Pro Asn Gly
            370                 375                 380

Asp Ala Glu Ala Asn Ala Ala Gly Gly Lys Pro Gly Met Glu Met
385                 390                 395                 400

Gly Lys Met Thr Gly Met Gly Met Gly Ala Gly Met Gly Met
            405                 410                 415

Ala Thr Ile Asp Ser Gly Arg Val Ile Leu Ala Val Pro Asp Ile Ser
            420                 425                 430

Met Val Asp Phe Phe Arg Glu Gln Phe Ala Arg Leu Pro Val Pro Tyr
            435                 440                 445

Glu Leu Val Pro Ala Leu Gly Ala Glu Asn Thr Leu Gln Leu Val Gln
        450                 455                 460

Gln Ala Gln Ser Leu Gly Cys Asp Phe Val Leu Met His Pro Glu
465                 470                 475                 480

Phe Leu Arg Asp Arg Ser Pro Thr Gly Leu Leu Pro Arg Leu Lys Met
                485                 490                 495

Gly Gly Gln Arg Ala Ala Ala Phe Gly Trp Ala Ala Ile Gly Pro Met
```

```
                      500             505             510
Arg Asp Leu Ile Glu Gly Ser Gly Val Asp Gly Trp Leu Glu Gly Pro
                515             520             525

Ser Phe Gly Ala Gly Ile Asn Gln Gln Ala Leu Val Ala Leu Ile Asn
            530                 535                 540

Arg Met Gln Gln Ala Lys Lys Met Gly Met Met Gly Gly Met Gly Met
545                 550                 555                 560

Gly Met Gly Gly Met Gly Met Gly Met Gly Met Gly Met Gly Met
                565                 570                 575

Ala Pro Ser Met Asn Ala Gly Met Thr Gly Gly Met Gly Gly Ala Ser
            580                 585                 590

Met Gly Gly Ala Val Met Gly Met Gly Met Gly Met Gln Pro Met Gln
            595                 600                 605

Gln Ala Met Pro Ala Met Ser Pro Met Met Thr Gln Gln Pro Ser Met
        610                 615                 620

Met Ser Gln Pro Ser Ala Met Ser Ala Gly Gly Ala Met Gln Ala Met
625                 630                 635                 640

Gly Gly Val Met Pro Ser Pro Ala Pro Gly Gly Arg Val Gly Thr Asn
                645                 650                 655

Pro Leu Phe Gly Ser Ala Pro Ser Pro Leu Ser Ser Gln Pro Gly Ile
            660                 665                 670

Ser Pro Gly Met Ala Thr Pro Pro Ala Ala Thr Ala Ala Pro Ala Ala
            675                 680                 685

Gly Gly Ser Glu Ala Glu Met Leu Gln Gln Leu Met Ser Glu Ile Asn
            690                 695                 700

Arg Leu Lys Asn Glu Leu Gly Glu
705                 710

<210> SEQ ID NO 4
<211> LENGTH: 2236
<212> TYPE: DNA
<213> ORGANISM: C. reinhardtii

<400> SEQUENCE: 4
gcgttgcttg actacgcttc gctgtaataa tagcagcgcc acaagtagtg tcgccaaaca      60
actctcactt tgagcttgag cacaccgctg agccccgatg tcgcggaggc catggcttct     120
tgccctagcg ctggcagtgg cgctggcggc cggcagcgca ggagcctcga ctggcagtga     180
cgcgacggtg ccggtcgcga ctcaggatgg ccccgactac gttttccacc gtgcccacga     240
gcgcatgctc ttccaaacct catacactct tgagaacaat ggttctgtta tttgcatccc     300
gaacaacggc cagtgcttct gcttggcttg cttaaatcc aacggaacaa atgccgagaa     360
gttggctgcc aacattctgc agtggattac ttttgcgctt tcagcgctct gcctgatgtt     420
ctacggctac cagacctgga gtctacttg cggctgggag gagatttacg tggccacgat     480
cgagatgatc aagttcatca tcgagtattt ccatgagttt gacgaacctg cggtgatcta     540
ctcatccaac ggcaacaaga ccgtgtggct tcgttacgcg gagtggctgc tgacctgccc     600
tgtcattctt atccatctga gcaaccttac gggtctggcg aacgactata caagcgtac      660 catgggtctg ctggtgtcag atatcggcac gatcgtgtgg ggcaccacgg ccgcgctgtc     720
caagggatac gtccgtgtca tttttcttcct gatgggcctg tgctacggca tctacacatt     780
cttcaacgca gccaaggtct acattgaggc gtaccacacc gtgcccaagg catttgccg      840 cgacctggtc cgctaccttg cctggctcta cttctgttca tgggctatgt tcccggtgct     900
```

```
gttcctgctg ggccccgagg gctttggcca catcaaccaa ttcaactctg ccatcgccca    960
cgccatcctg gaccttgcct ccaagaacgc ttggagtatg atgggtcact ttctgcgtgt   1020
caagatccac gagcacatcc tgctgtacgg cgacatccgc aagaagcaga aggtcaacgt   1080
ggctggccag gagatggagg tggagaccat ggtgcacgag gaggacgacg agacgcagaa   1140
ggtgcccacg gcaaagtacg ccaaccgcga ctcgttcatc atcatgcgcg accgcctcaa   1200
ggagaagggc ttcgagaccc gcgcctcgct ggacggcgac ccgaacgcg acgccgaggc   1260
caacgctgca gccggcggca agcccggaat ggagatgggc aagatgaccg gcatgggcat   1320
gggcatgggt gccggcatgg gcatggcgac catcgattcg ggccgcgtca tcctcgccgt   1380
gccggacatc tccatggtgg acttttttccg cgagcagttc gcgcggctgc ccgtgcccta   1440
cgaactggtg cccgcgctgg gcgcggagaa caccctccag ctggtgcagc aggcgcagtc   1500
actgggaggc tgcgacttcg tcctcatgca ccccgagttc ctgcgcgacc gcagtcccac   1560
gggtctgctg ccccgcctca agatgggcgg cagcgcgcc gcggccttcg gctgggcggc   1620
aatcggcccc atgcgggact tgatcgaggg ttcgggcgtt gacggctggc tggagggccc   1680
cagctttggc gccggcatca accagcaggc gctggtggcg ctgatcaacc gcatgcagca   1740
ggccaagaag atgggcatga tgggcggtat gggtatgggc atgggcggcg catgggtat   1800
gggcatgggt atgggcatgg gcatggcccc cagcatgaac gccggcatga ctggcggcat   1860
gggcggcgcc tccatgggcg gtgccgtgat gggcatgggc atgggcatgc agcccatgca   1920
gcaggctatg ccggccatgt cgcccatgat gactcagcag cccagcatga tgagtcagcc   1980
ctccgccatg agcgccggcg cgccatgca ggccatgggt ggcgtcatgc ccagccccgc   2040
ccccggcggc cgcgtgggca ccaacccgct gtttggctct cgcgccctctc cgctgagctc   2100
gcagcccggc atcagccctg catggcgac ccgccccgcc gccaccgccg cacccgccgc   2160
tggcggcagc gaggccgaga tgctgcagca gctgatgagc gagatcaacc gcctgaagaa   2220
cgagctgggc gagtaa                                                  2236
```

<210> SEQ ID NO 5
<211> LENGTH: 261
<212> TYPE: PRT
<213> ORGANISM: Archaebacteria

<400> SEQUENCE: 5

Met Leu Glu Leu Leu Pro Thr Ala Val Glu Gly Val Ser Gln Ala Gln
1               5                   10                  15

Ile Thr Gly Arg Pro Glu Trp Ile Trp Leu Ala Leu Gly Thr Ala Leu
            20                  25                  30

Met Leu Gly Thr Leu Tyr Phe Leu Val Lys Gly Met Gly Val Ser Asp
        35                  40                  45

Pro Asp Ala Lys Lys Phe Tyr Ala Ile Thr Thr Leu Val Pro Ala Ile
    50                  55                  60

Ala Phe Thr Met Tyr Leu Ser Met Leu Leu Gly Tyr Gly Leu Thr Met
65                  70                  75                  80

Val Pro Phe Gly Gly Glu Gln Asn Pro Ile Tyr Trp Ala Arg Tyr Ala
                85                  90                  95

Asp Trp Leu Phe Thr Thr Pro Leu Leu Leu Asp Leu Ala Leu Leu
            100                 105                 110

Val Asp Ala Asp Gly Thr Ile Leu Ala Leu Val Gly Ala Asp Gly
        115                 120                 125

Ile Met Ile Gly Thr Gly Leu Val Gly Ala Leu Thr Lys Val Tyr Ser

```
                130               135               140
Tyr Arg Phe Val Trp Trp Ala Ile Ser Thr Ala Ala Met Leu Tyr Ile
145                 150                 155                 160

Leu Tyr Val Leu Phe Phe Gly Phe Thr Ser Lys Ala Glu Ser Met Arg
                165                 170                 175

Pro Glu Val Ala Ser Thr Phe Lys Val Leu Arg Asn Val Thr Val Val
                180                 185                 190

Leu Trp Ser Ala Tyr Pro Val Val Trp Leu Ile Gly Ser Glu Gly Ala
                195                 200                 205

Gly Ile Val Pro Leu Asn Ile Glu Thr Leu Leu Phe Met Val Leu Asp
                210                 215                 220

Val Ser Ala Lys Val Gly Phe Gly Leu Ile Leu Leu Arg Glu Arg Ala
225                 230                 235                 240

Ile Phe Gly Glu Ala Glu Ala Pro Glu Pro Ser Ala Gly Asp Gly Ala
                245                 250                 255

Ala Ala Thr Ser Asp
                260

<210> SEQ ID NO 6
<211> LENGTH: 145
<212> TYPE: PRT
<213> ORGANISM: Archaebacteria

<400> SEQUENCE: 6

Ile Tyr Trp Ala Arg Tyr Ala Asp Trp Leu Phe Thr Thr Pro Leu Leu
1               5                   10                  15

Leu Leu Asp Leu Ala Leu Leu Val Asp Ala Asp Gln Gly Thr Ile Leu
                20                  25                  30

Ala Leu Val Gly Ala Asp Gly Ile Met Ile Gly Thr Gly Leu Val Gly
                35                  40                  45

Ala Leu Thr Lys Val Tyr Ser Tyr Arg Phe Val Trp Trp Ala Ile Ser
                50                  55                  60

Thr Ala Ala Met Leu Tyr Ile Leu Tyr Val Leu Phe Phe Gly Phe Thr
65                  70                  75                  80

Ser Lys Ala Glu Ser Met Arg Pro Glu Val Ala Ser Thr Phe Lys Val
                85                  90                  95

Leu Arg Asn Val Thr Val Val Leu Trp Ser Ala Tyr Pro Val Val Trp
                100                 105                 110

Leu Ile Gly Ser Glu Gly Ala Gly Ile Val Pro Leu Asn Ile Glu Thr
                115                 120                 125

Leu Leu Phe Met Val Leu Asp Val Ser Ala Lys Val Gly Phe Gly Leu
                130                 135                 140

Ile
145

<210> SEQ ID NO 7
<211> LENGTH: 148
<212> TYPE: PRT
<213> ORGANISM: C. reinhardtii

<400> SEQUENCE: 7

Val Gln Trp Leu Arg Tyr Ala Glu Trp Leu Leu Thr Cys Pro Val Ile
1               5                   10                  15

Leu Ile His Leu Ser Asn Leu Thr Gly Leu Ser Asn Asp Tyr Ser Arg
                20                  25                  30

Arg Thr Met Gly Leu Leu Val Ser Asp Ile Gly Thr Ile Val Trp Gly
```

-continued

```
                35                  40                  45
Ala Thr Ser Ala Met Ala Thr Gly Tyr Val Lys Val Ile Phe Phe Cys
            50                  55                  60

Leu Gly Leu Cys Tyr Gly Ala Asn Thr Phe Phe His Ala Ala Lys Ala
65              70                  75                      80

Tyr Ile Glu Gly Tyr His Thr Val Pro Lys Gly Arg Cys Arg Gln Val
                85                  90                  95

Val Thr Gly Met Ala Trp Leu Phe Phe Val Ser Trp Gly Met Phe Pro
            100                 105                 110

Ile Leu Phe Ile Leu Gly Pro Glu Gly Phe Gly Val Leu Ser Val Tyr
        115                 120                 125

Gly Ser Thr Val Gly His Thr Ile Ile Asp Leu Met Ser Lys Asn Cys
        130                 135                 140

Trp Gly Leu Leu
145
```

OPTICAL DEPOLARIZATION OF CARDIAC TISSUE

BACKGROUND

The heart is the center of a person's circulatory system. It includes an electro-mechanical system performing two major pumping functions. The left portions of the heart draw oxygenated blood from the lungs and pump it to the organs of the body to provide the organs with their metabolic needs for oxygen. The right portions of the heart draw deoxygenated blood from the organs and pump it into the lungs where the blood gets oxygenated. The body's metabolic need for oxygen increases with the body's physical activity level. The pumping functions are accomplished by contractions of the myocardium (heart muscles). In a normal heart, the sinoatrial node, the heart's natural pacemaker, generates electrical impulses, known as action potentials, that propagate through an electrical conduction system to various regions of the heart to excite myocardial tissues in these regions. Coordinated delays in the propagations of the action potentials in a normal electrical conduction system cause the various regions of the heart to contract in synchrony such that the pumping functions are performed efficiently.

A blocked or otherwise damaged electrical conduction system causes the myocardium to contract at a rhythm that is too slow, too fast, and/or irregular. Such an abnormal rhythm is generally known as arrhythmia. Arrhythmia reduces the heart's pumping efficiency and hence, diminishes the blood flow to the body. One type of arrhythmia is fibrillation, where the heart quivers instead of beating normally. For instance, atrial fibrillation (AF) is associated with an abnormal heart rhythm where the atria quivers. AF as a disease target represents a significant unmet need with a hospitalization growth rate of 16.7% over last 5 years. AF-related hospitalization charges contribute over $3 B annually to health care system expenditures. Treatments for arrhythmias include electrical therapy such as pacing and defibrillation therapies, ablation and drug therapies. Catheter based therapies for AF are destructive, dangerous, and highly variable. For example, the procedure takes on the average about 4 hours, and has at best 50-80% efficacy. Drug therapy has approximately 60% efficacy and sometimes is proarrhythmic. Moreover, preventive device therapy has been ineffective at suppressing atrial arrhythmias, and shocks are painful device-based therapy that has impacted patient acceptance of implantable cardiac devices (ICD's) both for atrial and ventricular defibrillation.

SUMMARY OF THE INVENTION

The invention provides a vector for use with an implantable light emitting device. The vector may include a transcriptional control element which is operably linked to an open reading frame for a light sensitive protein that forms part of a light sensitive ion channel or a light sensitive protein that activates a G-protein signaling cascade that in turn activates an ion channel. For instance, opsins are photosensitive proteins that activate G-protein signaling cascades which regulate ion channel opening. In one embodiment, the vector includes an open reading frame that encodes melanopsin (Opn4; FIG. 4), a light sensitive protein which can promote the depolarization of cells via endogenous G-protein-ion channel pathways. In one embodiment, the open reading frame encodes a protein that forms part of a light sensitive ion channel, e.g., a channel rhodopsin or a variant (normative) of a wild-type light sensitive ion channel protein, e.g., a variant that has one or more, for instance, 5, 10 or 20 substitutions, but preferably has less than 10% of positions substituted, including conservative and nonconservative substitutions, relative to the wild-type light sensitive ion channel protein. The one or more substitutions result in the variant light sensitive protein being sensitive to a different or shifted spectrum of light relative to the corresponding wild-type light sensitive protein. For instance, the variant protein may be a variant of a channel rhodopsin.

In one embodiment, the vector is introduced to mammalian cells ex vivo. In another embodiment, the vector is introduced to mammalian cells in vivo. In one embodiment, the vector is introduced to cardiac cells. In another embodiment, the vector is introduced to vascular smooth muscle cells, nerve cells of the heart or the vagus system, or aortic endothelial cells. In one embodiment, the vector is a recombinant adeno-associated virus vector, which, in one embodiment, is delivered to the atrium. Expression of photosensitive proteins, e.g., a channel rhodopsin (see, e.g., FIG. 2), bacterial rhodopsin (see, e.g. FIG. 6E), or a variant protein forming a light sensitive channel (e.g., SPARK; see FIG. 3), from vectors in cells such as cardiac cells, allows for light induced depolarization of tissue having those genetically altered (modified) cells. Expression of photosensitive proteins in vivo, such as those with rapid response times, e.g., from about 1 to about 100 ms, may be combined with light delivery and sensing devices to provide for a system for depolarization of cells in vivo. In one embodiment, the system is a nonelectrical defibrillation system useful to prevent or treat arrhythmias such as atrial and ventricular arrhythmias. However, the system may also be used for pacing, cardioversion, A-V conduction, bridging conduction gaps, and the like.

Thus, in one embodiment, a system is provided for expressing a light sensitive, recombinant protein in cells and regulating the activity of the light sensitive, recombinant protein using a light delivery device (light emitting device). In one embodiment, the system includes a light emitting device to induce depolarization of cells having the light sensitive, recombinant protein, and an arrhythmia detection device to control the activity of the light emitting device. The light emitting device may emit light at one or a plurality of wavelengths, e.g., in a particular spectral region or band which does not represent the spectrum emitted by white light. The delivery of light by the light emitting device in a mammal having cells that express the light sensitive, recombinant protein is of sufficient duration to ensure complete depolarization of cells within the targeted area. Such a system may provide for pain-free defibrillation events.

In one embodiment, the invention provides a channel rhodopsin (ChR; see FIGS. 6A-D) encoding vector that is stably introduced to cardiac tissue, such as atrial tissue, using gene therapy approaches, e.g., using viral vectors such as adenoviral or adeno-associated viral vectors or nonviral polymeric delivery vehicles having expression cassettes. In one embodiment, the vector is stably introduced to cardiac tissue. In one embodiment, the vector, such as a viral or plasmid vector, for instance an adeno-associated viral vector, transiently expresses the light sensitive protein, for instance, post-MI or post-surgery. In response to light of the appropriate wavelength(s), ChR promotes the depolarization of cells encoding ChR. In one embodiment, an Opn4 encoding vector is stably introduced to cardiac tissue using gene therapy approaches. In response to light of the appropriate wavelength(s), Opn4 promotes the depolarization of cells using endogenous G-protein pathways to gate a non-specific ion channel. Cardiac cells likely express all of the necessary cofactors (Gq alpha subunits, PLC, ion channels, etc.) in this G-protein signaling pathway or other genes may not be, however, other genes may be coexpressed to enhance the photosensitivity of cells having Opn4 or other photosensitive proteins.

In one embodiment, the light sensitive protein is activated by blue light, and the light emitting device delivers blue wavelengths of light (e.g., about 420 nm to about 485 nm). For instance, for melanopsin or a "blue shifted" photosensitive variant ion channel protein, the device may emit light of a wavelength from about 400 nm to about 490 nm, e.g., about 415 nm to about 485 nm, such as about 420 or about 480 nm, of light. For a light sensitive protein that is activated by red light or a "red shifted" photosensitive variant ion channel protein, the device may emit light of a wavelength of about 590 nm to about 620 nm. Light emission from the device is regulated by a control circuit which may be coupled to a detection circuit. When arrhythmia is detected, the control circuit activates the light emitting device, which in turn illuminates an area sufficient to depolarize all of the cells in the exposed area, for instance, in a given region of the heart. One advantage of such a system is that depolarization energies can be more evenly delivered than from an electrical component in which the shock field can vary depending on the location. Thus, the use of optical based pacing may result in a more uniform depolarization (depolarize more tissue simultaneously/uniformly), and may eliminate conditions that allow the cells to be effected by an aberrant trigger (i.e., premature atrial contractions). In another embodiment, the light emitting device emits a second (different) wavelength of light to return the membrane potential to that prior to depolarization, e.g., a SPARK-based system. In one embodiment, the light emitting device is placed epicardially, which may lessen optical quenching by blood components. In one embodiment, a light sensitive polyene may be administered, e.g., p-hydroxycinnamic acid, retinal or a retinal derivative. Retinal derivatives include but are not limited to 3,4-dehydroretinal, 13-ethylretinal, 9-dm-retinal, 3-hydroxyretinal, 4-hydroxyretinal, naphthylretinal; 3,7,11-trimethyl-dodeca-2,4,6,8,10-pentaenal; 3,7-dimethyl-deca-2,4,6,8-tetraenal; 3,7-dimethyl-octa-2,4,6-trienal; and 6-7, or 10-11 rotation-blocked retinals with 4-, 5-, 6- or 7-member ring bridges, and including a 10-12- five-member ring-bridged retinal, or other molecule.

In another embodiment, the system is employed to prevent arrhythmias.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 5 is a schematic illustrating alignment of bacterial rhodopsin (SEQ ID NO:6) and channel rhodopsin (SEQ ID NO:7). Residues in blue font are targets for spectral shifting for channel rhodopsin 2. Numbering is relative to the mature polypeptide sequence.

FIGS. 6A-E present A) Amino acid sequence of channel rhodopsin 2 (SEQ ID NO: 1). B) Nucleotide sequence encoding a ChR2 (SEQ ID NO:2). C) Amino acid sequence of ChR1 (SEQ ID NO:3). D) Nucleotide sequence encoding a ChR1 (SEQ ID NO:4). E) Amino acid sequence of a bacterial rhodopsin (SEQ ID NO:5).

DETAILED DESCRIPTION OF THE INVENTION

Definitions

Figure 1:
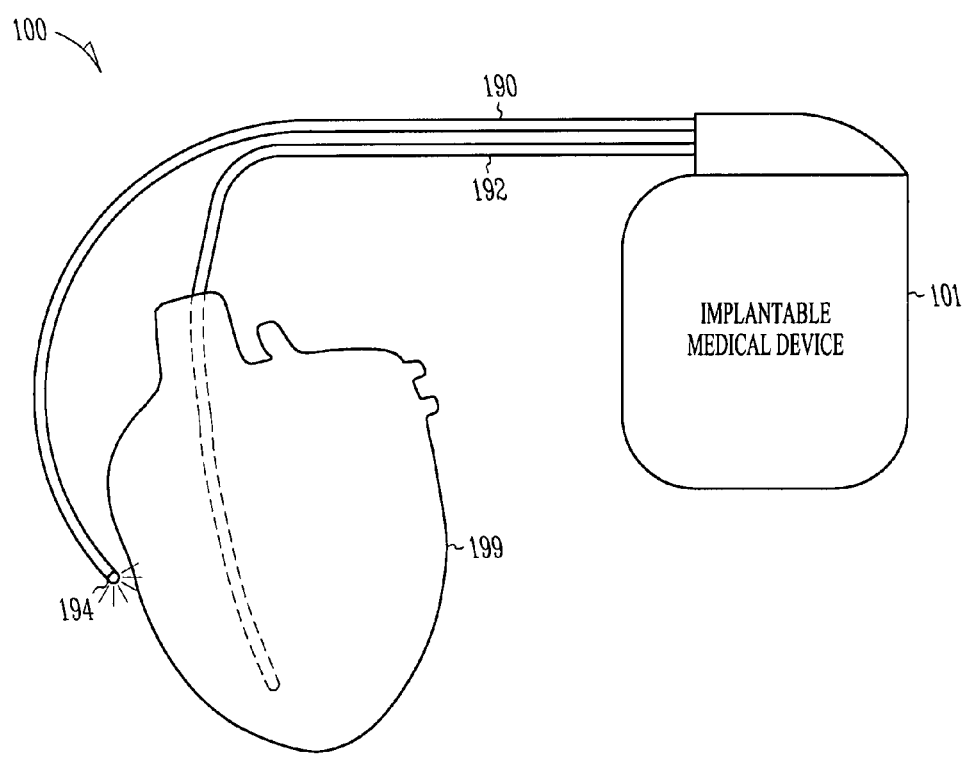
FIG. 1 is an illustration of an embodiment of an Optical Depolarization System (ODS) and portions of an environment in which the system operates.
Figure 2:
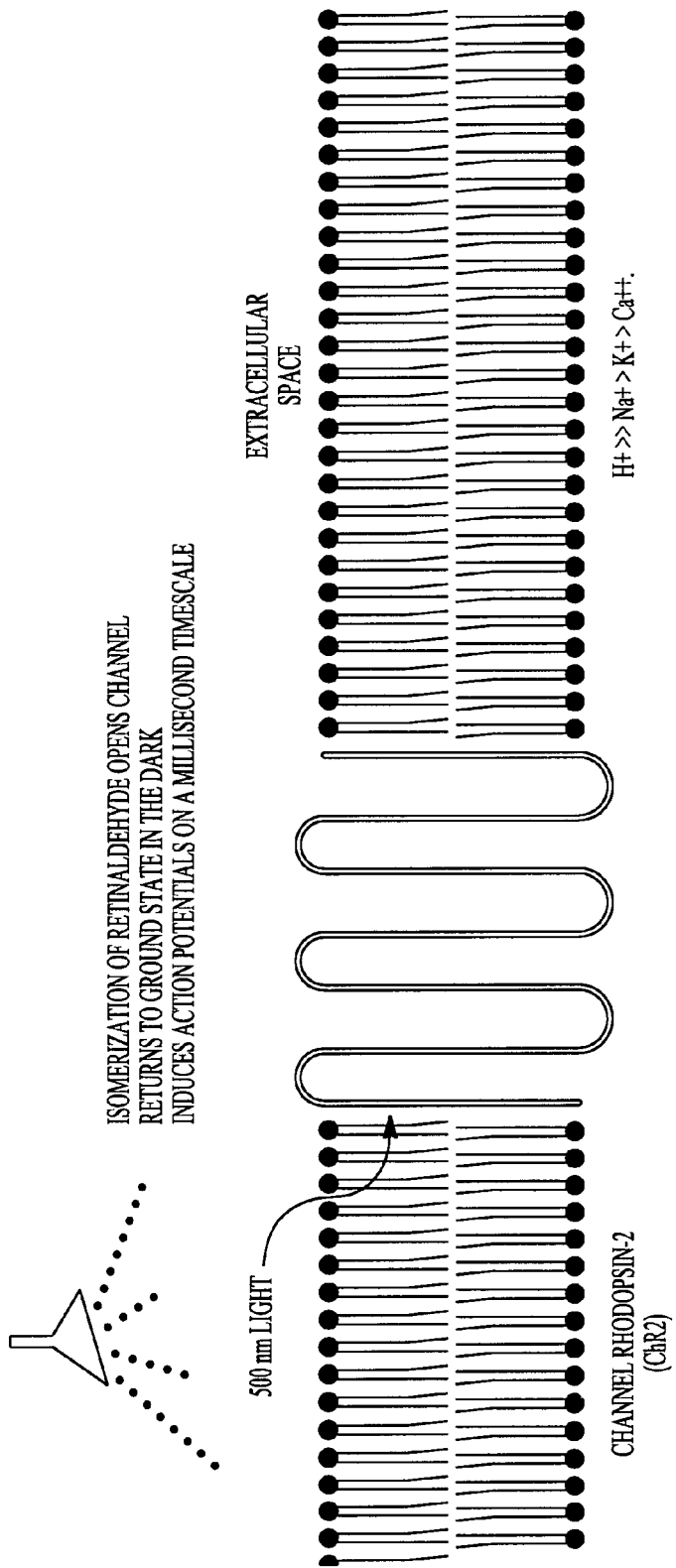
FIG. 2 is a schematic illustrating a light sensitive ion channel protein, e.g., a rhodopsin such as a channel rhodopsin-2 (ChR2). ChR2 has millisecond responses and may be useful for repeated cycling.
Figure 3:
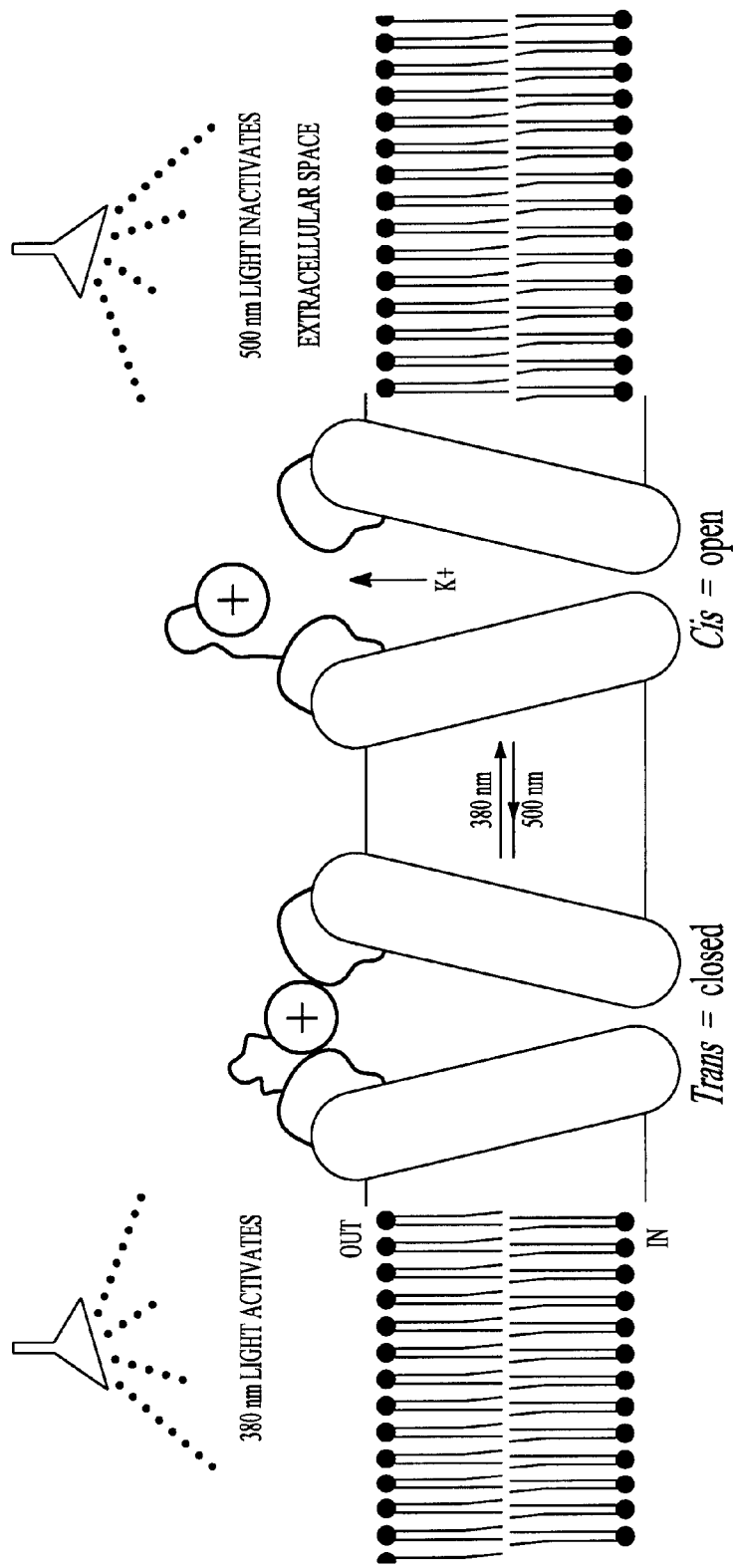
FIG. 3 is a schematic illustrating a light sensitive synthetic protein, SPARK.
Figure 4:
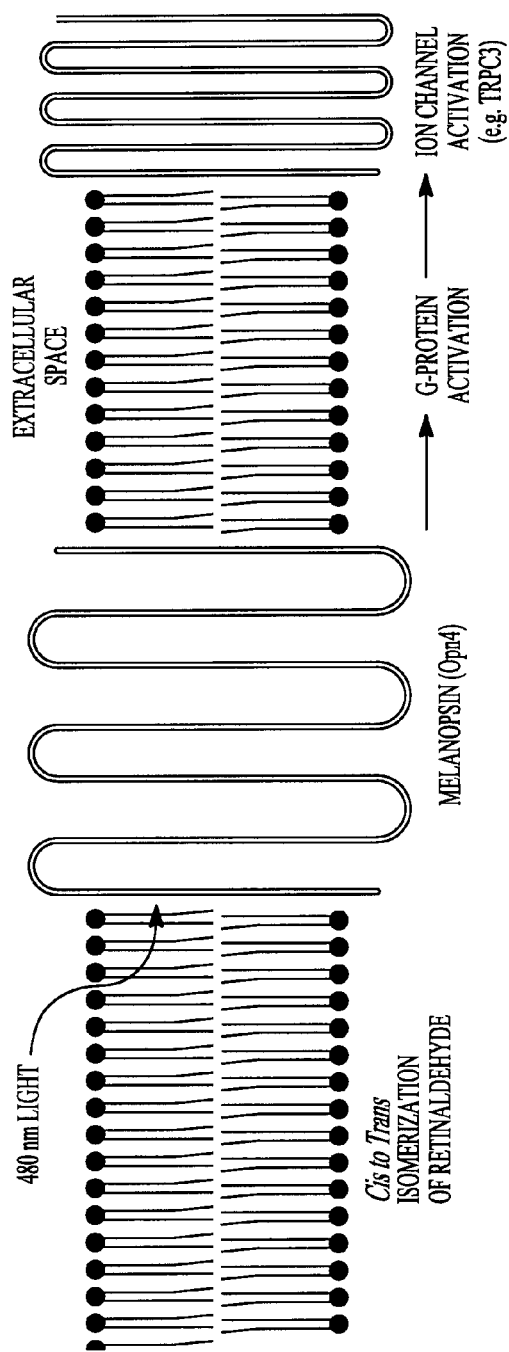
FIG. 4 is schematic illustrating a light sensitive protein that regulates G-protein associated with ion channel, e.g., melanopsin.

A "vector" or "construct" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a sequence of interest for gene therapy. Vectors include, for example, transposons and other site-specific mobile elements, viral vectors, e.g., adenovirus, adeno-associated virus (AAV), poxvirus, papillomavirus, lentivirus, herpesvirus, foamivirus and retrovirus vectors, and including pseudotyped viruses, liposomes and other lipid-containing complexes, and other macromolecular complexes capable of mediating delivery of a polynucleotide to a host cell, e.g., DNA coated gold particles, polymer-DNA complexes, liposome-DNA complexes, liposome-polymer-DNA complexes, virus-polymer-DNA complexes, e.g., adenovirus-polylysine-DNA complexes, and antibody-DNA complexes. Vectors can also comprise other components or functionalities that further modulate gene delivery and/or gene expression, or that otherwise provide beneficial properties to the cells to which the vectors will be introduced. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

A "recombinant viral vector" refers to a viral vector comprising one or more heterologous genes or sequences. Since many viral vectors exhibit size constraints associated with packaging, the heterologous genes or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying genes necessary for replication and/or encapsidation). Modified viral vectors in which a polynucleotide to be delivered is carried on the outside of the viral particle have also been described.

"Gene delivery," "gene transfer," and the like as used herein, are terms referring to the introduction of an exogenous polynucleotide (sometimes referred to as a "transgene"), e.g., via a recombinant virus, into a host cell or by a genetically modified donor cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, iontophoresis, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art.

By "transgene" is meant any piece of a nucleic acid molecule (for example, DNA) which is inserted by artifice into a cell either transiently or permanently, and becomes part of the cell if integrated into the genome or maintained extrachromosomally. Such a transgene may include a gene which is partly or entirely heterologous (i.e., foreign) to the transgenic organism, or may represent a gene homologous to an endogenous gene of the organism.

By "transgenic cell" or "genetically modified cell" is meant a cell containing a transgene. For example, a stem cell transformed with a vector containing an expression cassette can be used to produce a population of cells having altered phenotypic characteristics.

The term "wild-type" refers to a gene or gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "transduction" denotes the delivery of a polynucleotide to a recipient cell either in vivo or in vitro, via a viral vector and preferably via a replication-defective viral vector, such as via a recombinant AAV.

The term "heterologous" as it relates to nucleic acid sequences such as gene sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature, i.e., a heterologous promoter. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention.

By "DNA" is meant a polymeric form of deoxyribonucleotides (adenine, guanine, thymine, or cytosine) in double-stranded or single-stranded form found, inter alia, in linear DNA molecules (e.g., restriction fragments), viruses, plasmids, and chromosomes. In discussing the structure of particular DNA molecules, sequences may be described herein according to the normal convention of giving only the sequence in the 5' to 3' direction along the nontranscribed strand of DNA (i.e., the strand having the sequence complementary to the mRNA). The term captures molecules that include the four bases adenine, guanine, thymine, or cytosine, as well as molecules that include base analogues which are known in the art.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or polynucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation stimulations are located 3' or downstream of the coding region.

A "gene," "polynucleotide," "coding region," or "sequence" which "encodes" a particular gene product, is a nucleic acid molecule including codon optimized nucleic acid molecules (see, e.g., U.S. Pat. Nos. 5,874,304, 5,952,547 and 6,169,238, WO 97/47358, and PCT/US01/26566, the disclosures of which are incorporated by reference herein) which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. Thus, a gene includes a polynucleotide which may include a full-length open reading frame which encodes a gene product (sense orientation) or a portion thereof (sense orientation) which encodes a gene product with substantially the same activity as the gene product encoded by the full-length open reading frame, the complement of the polynucleotide, e.g., the complement of the full-length open reading frame (antisense orientation) and optionally linked 5' and/or 3' noncoding sequence(s) or a portion thereof, e.g., an oligonucleotide, which is useful to inhibit transcription, stability or translation of a corresponding mRNA. A transcription termination sequence will usually be located 3' to the gene sequence.

An "oligonucleotide" includes at least 7 nucleotides, preferably 15, and more preferably 20 or more sequential nucleotides, up to 100 nucleotides, either RNA or DNA, which correspond to the complement of the non-coding strand, or of the coding strand, of a selected mRNA, or which hybridize to the mRNA or DNA encoding the mRNA and remain stably bound under moderately stringent or highly stringent conditions, as defined by methods well known to the art, e.g., in Sambrook et al., A Laboratory Manual, Cold Spring Harbor Press (1989).

The term "control elements" refers collectively to promoter regions, polyadenylation stimulations, transcription termination sequences, upstream regulatory domains, origins of replication, internal ribosome entry sites ("IRES"), enhancers, splice junctions, and the like, which collectively provide for the replication, transcription, post-transcriptional processing and translation of a coding sequence in a recipient cell. Not all of these control elements need always be present so long as the selected coding sequence is capable of being replicated, transcribed and translated in an appropriate host cell.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence. Thus, a "promoter," refers to a polynucleotide sequence that controls transcription of a gene or coding sequence to which it is operably linked. A large number of promoters, including constitutive, inducible and repressible promoters, from a variety of different sources, are well known in the art.

By "enhancer element" is meant a nucleic acid sequence that, when positioned proximate to a promoter, confers increased transcription activity relative to the transcription activity resulting from the promoter in the absence of the enhancer domain. Hence, an "enhancer" includes a polynucleotide sequence that enhances transcription of a gene or coding sequence to which it is operably linked. A large number of enhancers, from a variety of different sources are well known in the art. A number of polynucleotides which have promoter sequences (such as the commonly-used CMV promoter) also have enhancer sequences.

"Operably linked" refers to a juxtaposition, wherein the components so described are in a relationship permitting them to function in their intended manner. By "operably linked" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. A promoter is operably linked to a coding sequence if the promoter controls transcription of the coding sequence. Although an operably linked promoter is generally located upstream of the coding sequence, it is not necessarily contiguous with it. An enhancer is operably linked to a coding sequence if the enhancer increases transcription of the coding sequence. Operably linked enhancers can be located upstream, within or downstream of coding sequences. A polyadenylation sequence is operably linked to a coding sequence if it is located at the downstream end of the coding sequence such that transcription proceeds through the coding sequence into the polyadenylation sequence. "Operably linked" with reference to peptide and/or polypeptide molecules is meant that two or more peptide and/or polypeptide molecules are connected in such a way as to yield a single polypeptide chain, i.e., a fusion polypeptide, having at least one property of each peptide and/or polypeptide component of the fusion. Thus, a stimulation or targeting peptide sequence is operably linked to another protein if the resulting fusion is secreted from a cell as a result of the presence of a secretory stimulation peptide or into an organelle as a result of the presence of an organelle targeting peptide.

"Homology" refers to the percent of identity between two polynucleotides or two polypeptides. The correspondence between one sequence and to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single strand-specific nuclease(s), and size determination of the digested fragments. Two DNA, or two polypeptide, sequences are "substantially homologous" to each other when at least about 80%, preferably at least about 90%, and most preferably at least about 95% of the nucleotides, or amino acids, respectively match over a defined length of the molecules, as determined using the methods above.

By "mammal" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like. An "animal" includes vertebrates such as mammals, avians, amphibians, reptiles and aquatic organisms including fish.

By "derived from" is meant that a nucleic acid molecule was either made or designed from a parent nucleic acid molecule, the derivative retaining substantially the same functional features of the parent nucleic acid molecule, e.g., encoding a gene product with substantially the same activity as the gene product encoded by the parent nucleic acid molecule from which it was made or designed.

By "expression construct" or "expression cassette" is meant a nucleic acid molecule that is capable of directing transcription. An expression construct includes, at the least, a promoter. Additional elements, such as an enhancer, and/or a transcription termination stimulation, may also be included.

The term "exogenous," when used in relation to a protein, gene or nucleic acid, e.g., polynucleotide, in a cell or organism refers to a protein, gene, or nucleic acid which has been introduced into the cell or organism by artificial or natural means, or in relation to a cell refers to a cell which was isolated and subsequently introduced to other cells or to an organism by artificial or natural means (a "donor" cell). An exogenous nucleic acid may be from a different organism or cell, or it may be one or more additional copies of a nucleic acid which occurs naturally within the organism or cell. An exogenous cell may be from a different organism, or it may be from the same organism. By way of a non-limiting example, an exogenous nucleic acid is in a chromosomal location different from that of natural cells, or is otherwise flanked by a different nucleic acid sequence than that found in nature.

The term "isolated" when used in relation to a nucleic acid, peptide, polypeptide or virus refers to a nucleic acid sequence, peptide, polypeptide or virus that is identified and separated from at least one contaminant nucleic acid, polypeptide, virus or other biological component with which it is ordinarily associated in its natural source. Isolated nucleic acid, peptide, polypeptide or virus is present in a form or setting that is different from that in which it is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid molecule may be present in single-stranded or double-stranded form. When an isolated nucleic acid molecule is to be utilized to express a protein, the molecule will contain at a minimum the sense or coding strand (i.e., the molecule may single-stranded), but may contain both the sense and anti-sense strands (i.e., the molecule may be double-stranded).

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "peptide", "polypeptide" and protein" are used interchangeably herein unless otherwise distinguished to refer to polymers of amino acids of any length. These terms also include proteins that are post-translationally modified through reactions that include glycosylation, acetylation and phosphorylation.

A "user" includes a patient, or a physician or other caregiver using a system of the invention to treat a patient.

"Red light" as used herein includes light of wavelengths longer than about 590 nm and less than about 730 nm, e.g., wavelengths of 610 nm to 650 nm. "Blue light" as used herein includes light of wavelengths greater than 400 nm to about 490 nm. For example, red light may correspond to a wavelength of 700 nm, a frequency of $4.29 \times 10^{14}$ Hz or 1.77 eV, as well as to a wavelength of 650 nm, a frequency of $4.62 \times 10^{14}$ Hz or 1.91 eV. Blue light may correspond to a wavelength of 450 nm, a frequency of $6.66 \times 10^{14}$ Hz or an energy of 2.75 eV.

"Depolarization" refers to a reduction in the absolute value of the membrane potential.

General Overview

The invention provides for devices, vectors, systems and methods to induce or enhance depolarization of cells. The system of the invention directly or indirectly induces conformational changes in ion channel components, for example, including conformational changes that either open or close the channel, with light or other energy (shock waves, radio frequencies, heat, ultrasound, and the like), thereby altering channel activity, which in turn regulates depolarization. A photosensitive ion channel protein or a photosensitive protein that regulates ion channels (or a vector encoding the protein or a host cell encoding the protein), a light emitting device and a detection circuit, is referred to herein as an optical depolarization system (ODS). In one embodiment, the photosensitive protein is an opsin. In one embodiment, the photosensitive protein is melanopsin. In another embodiment, the photosensitive protein is a channel rhodopsin. In yet another embodiment, the light sensitive protein is a bacterial rhodopsin. In one embodiment, a vector that encodes a protein that changes conformation after exposure to certain wavelengths of light, which conformational change alters ion channel or gap junction activity, is introduced to cells to yield genetically altered cells. The vector may encode a fusion of the light sensitive ion channel or other light sensitive protein and another protein, e.g., a human or synthetic protein. In one embodiment, the photosensitive protein may be targeted to intracellular organelles using, e.g., a fusion of the photosensitive protein with an intracellular targeting peptide, to modulate calcium mobilization (e.g., mimic ryanodine receptors) or modulate acidification of organelles (such as that associated with neurodegeneration, osteoporosis, and the like). In one embodiment, the photosensitive protein is expressed from a vector having a tissue specific promoter. In one embodiment, the photosensitive protein is expressed from a vector having an inducible promoter. In one embodiment, the photosensitive protein is expressed from a vector having a constitutive promoter. In one embodiment, other genes are expressed recombinantly, for instance, secondary signaling components within the opsin pathway (Gqα, arrestin, PLC, 11-cis-retinal, etc.), in conjunction with the light sensitive protein. The vector may be introduced to cells in vivo, or to cells ex vivo that may be preconditioned (e.g., via pacing, stretch, strain, hypoxia or growth factors) to promote a cardiac phenotype. In one embodiment, biocompatible polymers such as isolated extracellular matrix (ECM) or a hydrogel may be mixed with the vector or the genetically altered cells to form a gene delivery composition, such as a patch, which, in one embodiment, may be employed as a bridge for a conduction block.

In another embodiment, a photosensitive protein that forms part of or regulates ion channels, such as a recombinant opsin protein is delivered to the tissue (protein transfection). In another embodiment, expression of an endogenous photosensitive protein is upregulated.

The system also includes a light emitting device. For example, the light emitting device may include one or more LEDs to deliver a narrow wavelength of light. In one embodiment, the light emitting device includes a broad spectrum light source and a spectral filter. The light emitting device may be configured to deliver light to specific foci or across broad areas, or to deliver multifocal stimuli to span conduction blocks. Light delivered to broad areas in particular is useful in a system that provides for global depolarization of cardiac tissue to promote defibrillation. In one embodiment, the light emitting device is configured for epicardial placement. In one embodiment, the light emitting device is configured for endocardial placement. In one embodiment, the system includes a 2-dimensional patch having the light emitting device. In one embodiment, the light emitting device includes multiple light delivery sources (e.g., multiple heads or LED bions). In one embodiment, the system includes an arrhythmia detection system. Such a system may be used to defibrillate supraventricular tachycardias or ventricular tachycardias.

In one embodiment, the light emitting device triggers depolarization in a single or small foci within the cardiac wall. In one embodiment, the light emitting device triggers depolarization of multiple foci within the cardiac wall. In one embodiment, the light emitting device triggers depolarization of large regions within the cardiac wall. In one embodiment, besides the light emitting device, the system may include a pacing device to provide pacing rhythms. In one embodiment, besides the light emitting device, the system may include an electrical defibrillation device.

The system also includes a sensor to sense different cardiac states, including atrial and ventricular tachyarrhythmias, that can be regulated when the depolarizing optical pulse is delivered. Thus, applications for the system of the invention include treating atrial fibrillation, ventricular fibrillation, atrial or ventricular tachycardias, or providing for A-V conduction, prolonged refractory periods using longer pulses or suboptimal excitation (off-peak wavelengths), bridging conduction gaps, optionally in conjunction with pacing or the Maze procedure. A system of the invention may thus be employed to bridge conduction gaps, for cardioversion, or for A-V conduction. Light emission may be used to result in temporary, intermittent or prolonged depolarization (which may induce apoptosis), or both. For example, temporary light emission may be employed to test of sources for a fibrillation trigger and extended light emission may be used to induce apoptosis in cells that trigger fibrillation.

In one embodiment, for a device which delivers blue light, the light emitting device is placed in close proximity to the genetically altered cells, e.g., epicardially, as blue light does not penetrate as deeply as, for instance, red light. In one embodiment, to treat AF, a vector encoding a light sensitive protein which is sensitive to blue light is administer epicardially or systemically, and a light emitting device which emits blue light is placed epicardially. In one embodiment, to treat AF, a vector encoding a light sensitive protein which is sensitive to red light is administered and a light emitting device which emits red light is placed epicardially or in a blood vessel.

The system may be useful to treat a wide range of channelopathies in tissues or organs such as the heart, skeletal muscle, smooth muscle, kidney, ear, pancreas (insulin secretion), or nerves.

FIG. 1 is an illustration of an embodiment of an ODS 100 and portions of an environment in which ODS 100 operates. ODS 100 includes an implantable medical device 101 coupled to a heart 199 via an implantable sensing lead 192 and an implantable stimulation lead 190. Sensing lead 192 allows for the sensing of different cardiac states, including atrial and ventricular tachyarrhythmias, by implantable medical device 101. In one embodiment, the ODS includes multiple sensing leads. In one embodiment, multiple sensing leads allow for sensing RA, RV and/or LV states. Stimulation lead 190 provides for connection between a light emitting device 194 and implantable medical device 101. In the illustrated embodiment, stimulation lead 190 is an epicardial lead with light emitting device 194 configured for epicardial placement. In another embodiment, stimulation lead 190 includes an endocardial lead with light emitting device 194 configured for endocardial placement. In various embodiments, light emitting device 194 delivers light for depolarizing myocardial tissue of heart 199 for pacing and/or defibrillation. Embodiments of ODS are further discussed below with reference to FIGS. 7-13.

Exemplary Light Sensitive Proteins

Nonvisual photoresponses in mammals are generated in part by a network of cells that directly innervate the brain regions that mediate these responses (Ruby et al., *Science*, 298:2211 (2002); Hattar et al., *Science*, 295:1065 (2002); Hannibal et al., *J. Neurosci.*, 22:RC191 (2002); Gooley et al., *Nature Neurosic.*, 4:1165 (2001); Berson et al., *Science*, 295: 1070 (2002); Lucas et al., *Science*, 299:245 (2003); and Panda et al., *Science*, 298:2213 (2002)). The photosensitivity of these cells is dependent on melanopsin (Opn4) (Hattar et al., 2002; Berson et al., 2002; and Lucas et al., 2003), an atypical vertebrate opsin.

Vertebrate and invertebrate photosensitive opsins are heterotrimeric guanine nucleotide-binding protein (G-protein)-coupled receptors (GPCRs) that use 11-cis-retinaldehyde (11-cis-retinal) or a close variant as their chromophore (Hardie et al., *Nature*, 413:186 (2001)). Photoconversion of the 11-cis-retinal to all-trans-retinaldehyde (all-trans-retinal) creates a conformational change in these opsin proteins that triggers G-protein activation and subsequent signaling. Vertebrate rod-and-cone opsins signal through photoreceptor-specific, pertussis toxin (PTX)-sensitive G-proteins called transducins, whereas invertebrate opsins signal through the PTX-insensitive $G_q$ family of G proteins (Hardie et al., 2001; supra). These responses are terminated by a combination of phosphorylation of the excited opsin and the binding of arrestin proteins (Burns et al., *Annu. Rev. Neurosci.*, 24:779 (2001)). After signaling, regeneration of the active chromophore restores photosensitivity. In vertebrates, this process involves release of all-trans-retinal from the opsin and conversion back to 11-cis-retinal. Invertebrate opsins, such as *Drosophila* rhodopsin 1 (rhodopsin is composed of the protein opsin (about 50 kD in size) covalently linked to 11-cis-retinal (a derivative of vitamin A) through Lys296, instead photoconvert all-trans-retinal back to the active form in an arrestin-dependent manner (Kiselev et al., *Biochemistry*, 36:2188 (1997)) and so also function as photoisomerases, obviating the need for an accessory pigment regeneration mechanism. Sequence comparisons have shown the melanopsin shares significant similarity to opsins from invertebrates (Provencio et al., 1998), and therefore melanopsin may function more like an invertebrate opsin than vertebrate rod-and-cone opsins.

In one embodiment, the sensitization of cells to light when photostimulation is applied results in an intracellular increase of second messengers, including $IP_3$ and/or calcium ions. Also, by coupling photoactivation of rhodopsin to a G-protein alpha subunit other than the alpha subunit of $G_q$, one can elicit, through photostimulation, a response other than an increase in intracellular $IP_3$, $Ca^{2+}$, and DAG. For example, one may fuse rhodopsin to the alpha subunit of $G_s$ or $G_i$ instead of $G_q$. See Hamm et al., *Curr. Opin. Cell. Biol.*, 8:189 (1996); and Neer, *Cell*, 80:249 (1995).

Melanopsin activates $G_s$ which, in turn, activates adenylate cyclase (AC), which converts ATP to cAMP. cAMP, like $IP_3$ and DAG, is a cellular messenger that profoundly affects the biochemistry of those cells in which it is generated. $G_i$ counteracts the effect of $G_s$ by inactivating adenylate cyclase. Moreover, some $G_i$ proteins can open ion channels directly by binding to them.

To couple the pathways controlled by various G-protein subunits to rhodopsin activation, the alpha subunit of $G_q$ may be replaced with a chimeric subunit of a G protein. It has been found that the last 5 amino acids of a G-protein subtype are primarily responsible for specifying the receptor that activates that protein.

Voltage-gated K+ channels, including Shaker, are blocked by the binding of quaternary ammonium ions, such as tetraethylammonium (TEA), to a site in the pore-lining domain (MacKinnon et al., Science, 250:276 (1990); Heginbotham et al., Neuron, 8:483 (1992)). When a cysteine is substituted at position Glu422, which is estimated to be 15-18 Å from the TEA binding site, tethering of a series of cysteine-reactive compounds that contain quaternary ammonium to this positions shows that the degree of block is critically dependent on tether length, with a 5-Å difference in length making the distinction between effective and ineffective block (Blaustein et al., 2000). A photoswitchable blocker, e.g., MAL-AZO-QA, consists of a molecule (MAL) for cysteine tethering and a quaternary ammonium group to block the channel, and an azo group between, can be tethered to the outside of modified Shaker channels. The rigid azo moiety in MAL-AZO-Q A shortens by approximately 7 Å when photoisomerized from the trans to the cis configuration (Knoll, CRC Handbook of Organic Photochemistry and Photobiology, edn. 2 (eds. Horspool & Lenci) pg. 89.1 (CRC Press, Boca Raton, Fla. (2004)). Coupling MAL-AZO-QA to a cysteine introduced at residue 422 (mutant E422C) blocks channels when the compound is in the long trans form, whereas photoconversion to the cis configuration would make the tether too short to permit block. Hence tethering of MAL-AZO-QA to Shaker provides an extracellular gate that can be opened and closed with appropriate wavelengths of light.

In one embodiment, the vector encodes an apoprotein from lower eukaryotes. The group of the lower eukaryotes includes, for example, algae, protozoa, ciliates and yeasts. In one embodiment, the apoprotein is from motile green algae, in particular Chlorophyceae, such as apoproteins from Volvocales. In one embodiment, the apoprotein is an opsin protein from Chlamydomonas spp., e.g., C. reinhardtii. Further apoproteins include those from Ulvophytes such as Acetabularia and Ulva. In other embodiments, the opsins from Prasinophyceae, for example, Pyramimonas and Platymonas (Tetraselmis), or from the kingdom of the Dinophytes with the individual class of the Dinophyceae, for example, the members Gymnodinium splendens, Gyrodinium dorsum, Peridinium balticum and Gonyaulax.

In one embodiment, the photosensitive ion channel protein is derived from a protozoon, a bacterium or an archaebacterium. In one embodiment, the photosensitive ion channel protein is derived from fungi such as Neurospora crassa, Fusarium sporotrichioides and Leptosphaeria maculans, or Chytridiomyceten such as for example Allomyces reticulatus, or from ciliates such as Fabrea salina or Paramecium bursaria or from Foraminifera such as Amphistegina radiata.

Channel rhodopsins (ChRs) are microbial type rhodopsins with an intrinsic light-gated cation conductance. In one embodiment, the photosensitive protein is from C. reinhardtii, which forms passive ion transport systems, e.g., Channelopsin1 (ChR1 or CHOP-1) and Channelopsin2 (ChR2 or CHOP2). CHOP-1 protein has a molecular weight of 76 kD and a length of 712 amino acids. The core protein (amino acids 76-309) includes 7 hypothetical transmembrane segments with 15-20% homology to the sensory archaeal rhodopsins, the ion transporters bacteriorhodopsin (BR) and halorhodopsin (HR), and to a rhodopsin from the fungus Neurospora crassa (NOP1). The induced photocurrent and hence the ion transport of CHOP-1, CHOP-1 (1-346) and CHOP-1 (1-517) is dependent on the wavelength of the excitant light and reaches a maximum at 500 nm.

CHOP-2 has 737 amino acids and displays a homology of 52.7% to CHOP-1. The ion channel formed with CHOP-2 as apoprotein differs from that formed with CHOP-1 in terms of its unit conductivity, its inactivation under prolonged illumination and the shape of the current-voltage curve. Channelrhodopsin-2 (ChR2), which is made up of the protein Channelopsin-2 (CHOP-2) and retinal, and ChR2(1-315) are light-controlled cation channels, which are permeable for example to $Li^+$, $Na^+$, $K^+$, $Ba^{2+}$, $Sr^+$ and $Ca^{2+}$, but not to $Mg^{2+}$. The maximum for the excitant light lies at 440-480 nm.

ChR1 from Chlamydomonas reinhardii is specific for protons (Nagel et al., Science, 296:2395 (2002)), whereas ChR2 is a less selective cation channel with conductance for $H^+>>Na^+>K^+>Ca^{2+}$. Because the conductance of ChR2 is higher than that of ChR1, ChR2 and C terminally truncated versions of ChR2, e.g., ChR2(1-315) which are substantially as active as the full-length protein (Nagel et al., Proc. Natl. Acad. Sci. USA, 100:13940 (2003)), may be employed in the systems of the invention. Light activation of ChR2 may result in depolarizations of 10-25 mV within 10 ms, with repolarization occurring within 200 ms.

Variants

One or more of the residues of a light sensitive protein can be altered to yield a variant protein, so long as the variant is light sensitive. For example, ChR2 may be substituted at one or more residues of SEQ ID NO: 1 to result in a protein that is sensitive to light of a different wavelength or band relative to SEQ ID NO: 1. Some substitutions may be conservative. Conservative amino acid substitutions include, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid substitution also include groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide.

Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

The invention also envisions variants with non-conservative substitutions. Non-conservative substitutions entail exchanging a member of one of the classes described above for another.

Vectors

Vectors useful in the systems and methods of include, for example, viral vectors, liposomes and other lipid-containing complexes, and other macromolecular complexes capable of mediating delivery of a gene to a host cell. Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector by the cell; components that influence localization of the transferred gene within the cell after uptake (such as agents mediating nuclear localization); and components that influence expression of the gene. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e., positive/negative) markers (see, e.g., WO 92/08796; and WO 94/28143). Such marker genes can provide an added measure of control that can be advantageous in gene delivery contexts. A large variety of such vectors are known in the art and are generally available.

Gene delivery vectors within the scope of the invention include, but are not limited to, isolated nucleic acid, e.g., plasmid-based vectors which may be extrachromosomally maintained, and viral vectors, e.g., recombinant adenovirus, retrovirus, lentivirus, herpesvirus, poxvirus, papilloma virus, or adeno-associated virus, including viral and non-viral vectors which are present in liposomes, e.g., neutral or cationic liposomes, such as DOSPA/DOPE, DOGS/DOPE or DMRIE/DOPE liposomes, and/or associated with other molecules such as DNA-anti-DNA antibody-cationic lipid (DOTMA/DOPE) complexes. Exemplary gene delivery vectors are described below. Vectors may be administered via any route including, but not limited to, intramuscular, buccal, rectal, intravenous or intracoronary administration, and transfer to cells may be enhanced using electroporation and/or iontophoresis.

Retroviral Vectors

Retroviral vectors exhibit several distinctive features including their ability to stably and precisely integrate into the host genome providing long-term transgene expression. These vectors can be manipulated ex vivo to eliminate infectious gene particles to minimize the risk of systemic infection and patient-to-patient transmission. Pseudotyped retroviral vectors can alter host cell tropism.

Lentiviruses

Lentiviruses are derived from a family of retroviruses that include human immunodeficiency virus and feline immunodeficiency virus. However, unlike retroviruses that only infect dividing cells, lentiviruses can infect both dividing and nondividing cells. For instance, lentiviral vectors based on human immunodeficiency virus genome are capable of efficient transduction of cardiac myocytes in vivo. Although lentiviruses have specific tropisms, pseudotyping the viral envelope with vesicular stomatitis virus yields virus with a broader range (Schnepp et al., *Meth. Mol. Med.,* 69:427 (2002)).

Adenoviral Vectors

Adenoviral vectors may be rendered replication-incompetent by deleting the early (E1A and E1B) genes responsible for viral gene expression from the genome and are stably maintained into the host cells in an extrachromosomal form. These vectors have the ability to transfect both replicating and nonreplicating cells and, in particular, these vectors have been shown to efficiently infect cardiac myocytes in vivo, e.g., after direction injection or perfusion. Adenoviral vectors have been shown to result in transient expression of therapeutic genes in vivo, peaking at 7 days and lasting approximately 4 weeks. The duration of transgene expression may be improved in systems utilizing cardiac specific promoters. In addition, adenoviral vectors can be produced at very high titers, allowing efficient gene transfer with small volumes of virus.

Adeno-associated Virus Vectors

Recombinant adeno-associated viruses (rAAV) are derived from nonpathogenic parvoviruses, evoke essentially no cellular immune response, and produce transgene expression lasting months in most systems. Moreover, like adenovirus, adeno-associated virus vectors also have the capability to infect replicating and nonreplicating cells and are believed to be nonpathogenic to humans. Moreover, they appear promising for sustained cardiac gene transfer (Hoshijima et al., *Nat. Med.,* 8:864 (2002); Lynch et al., *Circ. Res.,* 80:197 (1997)).

Herpesvirus/Amplicon

Herpes simplex virus 1 (HSV-1) has a number of important characteristics that make it an important gene delivery vector in vivo. There are two types of HSV-1-based vectors: 1) those produced by inserting the exogenous genes into a backbone virus genome, and 2) HSV amplicon virions that are produced by inserting the exogenous gene into an amplicon plasmid that is subsequently replicated and then packaged into virion particles. HSV-1 can infect a wide variety of cells, both dividing and nondividing, but has obviously strong tropism towards nerve cells. It has a very large genome size and can accommodate very large transgenes (>35 kb). Herpesvirus vectors are particularly useful for delivery of large genes, e.g., genes encoding ryanodine receptors and titin.

Plasmid DNA Vectors

Plasmid DNA is often referred to as "naked DNA" to indicate the absence of a more elaborate packaging system. Direct injection of plasmid DNA to myocardial cells in vivo has been accomplished. Plasmid-based vectors are relatively nonimmunogenic and nonpathogenic, with the potential to stably integrate in the cellular genome, resulting in long-term gene expression in postmitotic cells in vivo. For example, expression of secreted angiogenesis factors after muscle injection of plasmid DNA, despite relatively low levels of focal transgene expression, has demonstrated significant biologic effects in animal models and appears promising clinically (Isner, *Nature,* 415:234 (2002)). Furthermore, plasmid DNA is rapidly degraded in the blood stream; therefore, the chance of transgene expression in distant organ systems is negligible. Plasmid DNA may be delivered to cells as part of a macromolecular complex, e.g., a liposome or DNA-protein complex, and delivery may be enhanced using techniques including electroporation.

Transcriptional Control Elements

A device of the invention may deliver one or more signals including light of a particular wavelength or a range of wavelengths, or light of a particular energy, and also, optionally, acoustic energy, an electric field, a chemical, electromagnetic energy, thermal energy or other forms of temperature or matter. At least one of the signals delivered by the device controls the activity of a light sensitive protein encoded by a vector.

In one embodiment, the expression of the light sensitive protein is via a constitutive promoter. Alternatively, a variety of strategies have been devised to control in vivo expression of transferred genes and thus alter the pharmacokinetics of in vivo gene transfer vectors in the context of regulatable or inducible promoters. Many of these regulatable promoters use exogenously administered agents to control transgene expression and some use the physiologic milieu to control gene expression. Examples of the exogenous control promoters include the tetracycline-responsive promoter, a chimeric transactivator consisting of the DNA and tetracycline-binding domains from the bacterial tet repressor fused to the transactivation domain of herpes simplex virion protein 16 (Ho et al., *Brain Res. Mol. Brain Res.*, 41:200 (1996)); a chimeric promoter with multiple cyclic adenosine monophosphate response elements superimposed on a minimal fragment of the 5'-flanking region of the cystic fibrosis transmembrane conductance regulator gene (Suzuki et al., 7:1883 (1996)); the EGR1 radiation-inducible promoter (Hallahan et al., *Nat. Med.*, 1:786 (1995)); and the chimeric GRE promoter (Lee et al., *J. Thoracic Cardio. Surg.*, 118:26 (1996)), with 5 GREs from the rat tyrosine aminotransferase gene in tandem with the insertion of Ad2 major late promoter TATA box-initiation site (Narumi et al., *Blood*, 92:812 (1998)). Examples of the physiologic control of promoters include a chimera of the thymidine kinase promoter and the thyroid hormone and retinoic acid-responsive element responsive to both exogenous and endogenous tri-iodothyronine (Hayashi et al., *J. Biol. Chem.*, 269:23872 (1994)); complement factor 3 and serum amyloid A3 promoters responsive to inflammatory stimuli; the grp78 and BiP stress-inducible promoter, a glucose-regulated protein that is inducible through glucose deprivation, chronic anoxia, and acidic pH (Gazit et al., *Cancer Res.*, 55:1660 (1995)); and hypoxia-inducible factor 1 and a heterodimeric basic helix-loop-helix protein that activates transcription of the human erythropoietin gene in hypoxic cells, which has been shown to act as a regulatable promoter in the context of gene therapy in vivo (Forsythe et al., *Mol. Cell Biol.*, 16:4604 (1996)).

Regulatable transcriptional elements useful in vectors and methods of the invention include, but are not limited to, a truncated ligand binding domain of a progesterin receptor (controlled by antiprogestin), a tet promoter (controlled by tet and dox) (Dhawan et al., *Somat. Cell. Mol. Genet.*, 21, 233 (1995); Gossen et al., *Science*, 268:1766 (1995); Gossen et al., *Science*, 89:5547 (1992); Shockett et al., *Proc. Natl. Acad. Sci. USA*, 92, 6522 (1995)), hypoxia-inducible nuclear factors (Semenza et al., *Proc. Natl. Acad. Sci. USA*, 88, 5680 (1991); Semenza et al., *J. Biol. Chem.*, 269, 23757)), steroid-inducible elements and promoters, such as the glucocorticoid response element (GRE) (Mader and White, *Proc. Natl. Acad. Sci. USA*, 90, 5603 (1993)), and the fusion consensus element for RU486 induction (Wang et al., *Proc. Natl. Acad. Sci. USA*, 91:818 (1994)), those sensitive to electromagnetic fields, e.g., those present in metallothionein I or II, c-myc, and HSP70 promoters (Lin et al., *J. Cell. Biochem.*, 81:143 (2001); Lin et al., *J. Cell. Biochem.*, 54:281 (1994); U.S. published application 20020099026)), and electric pulses (Rubenstrunk et al., *J. Gene Med.*, 5:773 (2003)), as well as a yeast GAL4/TATA promoter, auxin inducible element, an ecdysone responsive element (No et al., *Proc. Natl. Acad. Sci. USA*, 93:3346 (1996)), an element inducible by rapamycin (FK506) or an analog thereof (Rivera et al., *Nat. Med.*, 2:1028 (1996); Ye et al., *Science*, 283:88 (1999); Rivera et al., *Proc. Natl. Acad. Sci. USA*, 96:8657 (1999)), a tat responsive element, a metal, e.g., zinc, inducible element, a radiation inducible element, e.g., ionizing radiation has been used as the inducer of the promoter of the early growth response gene (Erg-1) (Hallahan et al., *Nat. Med.*, 1:786 (1995)), an element which binds nuclear receptor PPARγ (peroxisome proliferators activated receptors), which is composed of a minimal promoter fused to PPRE (PPAR responsive elements, see WO 00/78986), a cytochrome P450/A1 promoter, a MDR-1 promoter, a promoter induced by specific cytokines (Varley et al., *Nat. Biotech.*, 15:1002 (1997)), a light inducible element (Shimizu-Sato et al., *Nat. Biotech.*, 20:1041 (2002)), a lacZ promoter, and a yeast Leu3 promoter.

In some embodiments, cell- or tissue-specific control elements, such as muscle-specific and inducible promoters, enhancers and the like, may be of particular use. Such control elements include, but are not limited to, those derived from the actin and myosin gene families, such as from the myoD gene family (Weintraub et al., *Science*, 251, 761 (1991)); the myocyte-specific enhancer binding factor MEF-2 (Cserjesi and Olson, *Mol. Cell Biol.*, 11, 4854 (1991)); control elements derived from the human skeletal actin gene (Muscat et al., *Mol. Cell Bio.*, 7, 4089 (1987)) and the cardiac actin gene; muscle creatine kinase sequence elements (Johnson et al., *Mol. Cell Biol.*, 9, 3393 (1989)) and the murine creatine kinase enhancer (mCK) element; control elements derived from the skeletal fast-twitch troponin C gene, the slow-twitch cardiac troponin C gene and the slow-twitch troponin I genes.

Cardiac cell restricted promoters include but are not limited to promoters from the following genes: a α-myosin heavy chain gene, e.g., a ventricular α-myosin heavy chain gene, β-myosin heavy chain gene, e.g., a ventricular β-myosin heavy chain gene, myosin light chain 2v gene, e.g., a ventricular myosin light chain 2 gene, myosin light chain 2a gene, e.g., a ventricular myosin light chain 2 gene, cardiomyocyte-restricted cardiac ankyrin repeat protein (CARP) gene, cardiac α-actin gene, cardiac m2 muscarinic acetylcholine gene, ANP gene, BNP gene, cardiac troponin C gene, cardiac troponin I gene, cardiac troponin T gene, cardiac sarcoplasmic reticulum Ca-ATPase gene, skeletal α-actin gene, as well as an artificial cardiac cell-specific promoter.

Further, chamber-specific promoters or enhancers may also be employed, e.g., for atrial-specific expression, the quail slow myosin chain type 3 (MyHC3) or ANP promoter, or the cGATA-6 enhancer, may be employed. For ventricle-specific expression, the iroquois homeobox gene may be employed. Examples of ventricular myocyte-specific promoters include a ventricular myosin light chain 2 promoter and a ventricular myosin heavy chain promoter.

In other embodiments, disease-specific control elements may be employed. Thus, control elements from genes associated with a particular disease, including but not limited to any of the genes disclosed herein may be employed in vectors of the invention.

Nevertheless, other promoters and/or enhancers which are not specific for cardiac cells or muscle cells, e.g., RSV promoter, may be employed in the expression cassettes and methods of the invention. Other sources for promoters and/or enhancers are promoters and enhancers from the Csx/NKX 2.5 gene, titin gene, α-actinin gene, myomesin gene, M protein gene, cardiac troponin T gene, RyR2 gene, Cx40 gene, and Cx43 gene, as well as genes which bind Mef2, dHAND, GATA, CarG, E-box, Csx/NKX 2.5, or TGF-beta, or a combination thereof.

The response of the light sensitive protein to one or more intermittent light emissions, a prolonged light emission, or different levels of light emission, may be tested in vitro or in vivo. The vector may include a transcriptional control element linked to a marker gene, i.e., one which is readily detectable or capable of detection such as green fluorescent protein (GFP) fused to the light sensitive protein. The resulting expression cassette, e.g., one which is introduced to an adenovirus vector or to a plasmid vector, is employed to infect or transfect murine cells, e.g., murine cardiac cells, or heart sections. A system designed for use in a small flask is used to deliver light. Then fluorescence in the cells or a lysate thereof is detected, and/or vector specific RNA or protein is measured, for instance, using RT-PCR or immunoassays, respectively, and/or depolarization of the cells is detected, and optionally compared to data from control cells. Vectors may also be introduced to a non-human large animal model, e.g., pigs, to determine the level and spatial expression of the exogenously introduced gene in response to signals, from an implantable device in that animal. See, e.g., PCT/EP03/03799 and Boyden et al., Nat. Neuro., 8:1263 (2005).

Vector or Recombinant Cell Delivery

Isolated DNA, recombinant virus or recombinant cells encoding a light sensitive protein may be administered intravenously, transvenously, intramyocardially or by any other convenient route, and delivered by a needle, catheter, e.g., a catheter which includes an injection needle or infusion port, lead, or other suitable device. Generally any route of administration may be employed, including oral, mucosal, intramuscular, buccal and rectal administration. For certain vectors, certain routes of administration may be preferred. For instance, viruses, e.g., pseudotyped virus, and DNA- or virus-liposome, e.g., HVJ-liposome, may be administered by coronary infusion, while HVJ-liposome complexes may be delivered pericardially. Recombinant cells may also be delivered systemically, e.g., intravenously, transvenously, intramyocardially or by any other convenient route, and delivered by a needle, catheter, e.g., a catheter which includes an injection needle or infusion port, or other suitable device.

Several techniques have been developed for cardiac gene delivery, including pericardial infusion, endomyocardial injection, intracoronary injection, coronary venous retroperfusion, and aortic root injection (Isner, Nature, 415:234 (2002)). The different techniques achieve variable response in homogeneity of gene delivery, resulting in focal gene expression within the heart (Hajjar et al., Circ. Res., 86:616 (2000). For this reason, techniques that achieve diffuse uptake would seem to be superior. Two such methods utilize the heart's arterial and venous circulation to accomplish disseminated viral transfection. Arterial injection, performed directly through a percutaneous approach or indirectly by an infusion into the cross-clamped aorta, has shown promise in animal models of heart failure and is appealing in that it can be performed either at the time of cardiac surgery or as percutaneous intervention (Hajjar et al., PNAS USA, 95:5251 (1998)). Similarly, retroperfusion through the coronary sinus appears to produce a more global gene expression in comparison with techniques of localized or focal injection (Boeckstegers et al., Circ., 100:1 (1999)).

Direct Myocardial Injection

Direct myocardial injection of plasmid DNA as well as virus vectors, e.g., adenoviral vectors, and cells including recombinant cells has been documented in a number of in vivo studies. This technique when employed with plasmid DNA or adenoviral vectors has been shown to result in effective transduction of cardiac myocytes. Thus, direct injection may be employed as an adjunct therapy in patients undergoing open-heart surgery or as a stand-alone procedure via a modified thorascope through a small incision. Virus, e.g., pseudotyped, or DNA- or virus-liposome complexes may be delivered intramyocardially.

Catheter-based Delivery

Intracoronary delivery of genetic material can result in transduction of approximately 30% of the myocytes predominantly in the distribution of the coronary artery. Parameters influencing the delivery of vectors via intracoronary perfusion and enhancing the proportion of myocardium transduced include a high coronary flow rate, longer exposure time, vector concentration, and temperature. Gene delivery to a substantially greater percent of the myocardium may be enhanced by administering the gene in a low-calcium, high-serotonin mixture (Donahue et al., Nat. Med., 6:1395 (2000)). The potential use of this approach for gene therapy for heart failure may be increased by the use of specific proteins that enhance myocardial uptake of vectors (e.g., cardiac troponin T).

Improved methods of catheter-based gene delivery have been able to achieve almost complete transfection of the myocardium in vivo. Hajjar et al. (Proc. Natl. Acad. Sci. USA, 95:5251 (1998)) used a technique combining surgical catheter insertion through the left ventricular apex and across the aortic valve with perfusion of the gene of interest during cross-clamping of the aorta and pulmonary artery. This technique resulted in almost complete transduction of the heart and could serve as a protocol for the delivery of adjunctive gene therapy during open-heart surgery when the aorta can be cross-clamped.

Recombinant cells may also be delivered via catheter.

Pericardial Delivery

Gene delivery to the ventricular myocardium by injection of genetic material into the pericardium has shown efficient gene delivery to the epicardial layers of the myocardium. However, hyaluronidase and collagenase may enhance transduction without any detrimental effects on ventricular function. Recombinant cells may also be delivered pericardially.

Intravenous Delivery

Intravenous gene delivery may be efficacious for myocardial gene delivery. However, to improve targeted delivery and transduction efficiency of intravenously administered vectors, targeted vectors may be employed. In one embodiment, intravenous administration of DNA-liposome or antibody-DNA complexes may be employed.

Lead-based Delivery

Gene delivery can be performed by incorporating a gene delivery device or lumen into a lead such as a pacing lead, defibrillation lead, or pacing-defibrillation lead. An endocardial lead including a gene delivery device or lumen allows gene delivery to the endocardial layers of the myocardium. An epicardial lead including a gene delivery device or lumen allows gene delivery to the endocardial layers of the myocardium. A transvenous lead including a gene delivery device or lumen may also allow intravenous gene delivery.

In one embodiment, administration may be by intracoronary injection to one or both coronary arteries (or to one or more saphenous vein or internal mammary artery grafts or other conduits) using an appropriate coronary catheter. A variety of catheters and delivery routes can be used to achieve intracoronary delivery, as is known in the art. For example, a variety of general purpose catheters, as well as modified catheters, suitable for use in the present invention are available from commercial suppliers. Also, where delivery to the myocardium is achieved by injection directly into a coronary artery, a number of approaches can be used to introduce a catheter into the coronary artery, as is known in the art. By way of illustration, a catheter can be conveniently introduced into a femoral artery and threaded retrograde through the iliac artery and abdominal aorta and into a coronary artery. Alternatively, a catheter can be first introduced into a brachial or carotid artery and threaded retrograde to a coronary artery. Detailed descriptions of these and other techniques can be found in the art (see, e.g., above, including: Topol, (ed.), *The Textbook of Interventional Cardiology*, 4th Ed. (Elsevier 2002); Rutherford, *Vascular Surgery*, 5th Ed. (W. B. Saunders Co. 2000); Wyngaarden et al. (eds.), *The Cecil Textbook of Medicine*, 22nd Ed. (W. B. Saunders, 2001); and Sabiston, *The Textbook of Surgery*, 16th Ed. (Elsevier 2000)). By way of illustration, liposomes and other lipid-containing gene delivery complexes can be used to deliver one or more expression cassettes. The principles of the preparation and use of such complexes for gene delivery have been described in the art (see, e.g., Ledley, *Human Gene Therapy*, 6:1129 (1995); Miller et al., *FASEB Journal*, 9:190 (1995); Chonn et al., *Curr. Opin. Biotech.*, 6:698 (1995); Schofield et al., *British Med. Bull.*, 51:56 (1995); Brigham et al., *J. Liposome Res.*, 3:31 (1993)).

Administration of an expression cassette in a vector in accordance with the present invention may be continuous or intermittent, depending, for example, upon the recipient's physiological condition, whether the purpose of the administration is therapeutic or prophylactic, and other factors known to skilled practitioners. The administration of the expression cassette may be essentially continuous over a preselected period of time or may be in a series of spaced doses. Both local and systemic administration is contemplated. In one embodiment, local administration is contemplated.

Targeted Vectors

The present invention contemplates the use of cell targeting not only by delivery of the transgene or recombinant cell into the coronary artery, for example, but also by use of targeted vector constructs having features that tend to target gene delivery and/or gene expression to particular host cells or host cell types (such as the myocardium). Such targeted vector constructs would thus include targeted delivery vectors and/or targeted vectors, as described herein. Restricting delivery and/or expression can be beneficial as a means of further focusing the potential effects of gene therapy. The potential usefulness of further restricting delivery/expression depends in large part on the type of vector being used and the method and place of introduction of such vector. For instance, delivery of viral vectors via intracoronary injection to the myocardium has been observed to provide, in itself, highly targeted gene delivery. In addition, using vectors that do not result in transgene integration into a replicon of the host cell (such as adenovirus and numerous other vectors), cardiac myocytes are expected to exhibit relatively long transgene expression since the cells do not undergo rapid turnover. In contrast, expression in more rapidly dividing cells would tend to be decreased by cell division and turnover. However, other means of limiting delivery and/or expression can also be employed, in addition to or in place of the illustrated delivery method, as described herein.

Targeted delivery vectors include, for example, vectors (such as viruses, non-viral protein-based vectors and lipid-based vectors) having surface components (such as a member of a ligand-receptor pair, the other half of which is found on a host cell to be targeted) or other features that mediate preferential binding and/or gene delivery to particular host cells or host cell types. As is known in the art, a number of vectors of both viral and non-viral origin have inherent properties facilitating such preferential binding and/or have been modified to effect preferential targeting (see, e.g., Miller, et al., *FASEB Journal*, 9:190 (1995); Chonn et al., *Curr. Opin. Biotech.*, 6:698 (1995); Schofield et al., *British Med. Bull.*, 51:56 (1995); Schreier, *Pharmaceutica Acta Helvetiae*, 68:145 (1994); Ledley, *Human Gene Therapy*, 6:1129 (1995); WO 95/34647; WO 95/28494; and WO 96/00295).

Targeted vectors include vectors (such as viruses, non-viral protein-based vectors and lipid-based vectors) in which delivery results in transgene expression that is relatively limited to particular host cells or host cell types. For example, transgenes can be operably linked to heterologous tissue-specific enhancers or promoters thereby restricting expression to cells in that particular tissue. For example, tissue-specific transcriptional control sequences derived from a gene encoding left ventricular myosin light chain-2 ($MLC_2V$) or myosin heavy chain (MHC) can be fused to a transgene within a vector. Expression of the transgene can therefore be relatively restricted to ventricular cardiac myocytes.

Dosages and Dosage Forms

The amount of vector(s), e.g., those which are present in a recombinant cell or in acellular form, administered and device based signal emitted to achieve a particular outcome will vary depending on various factors including, but not limited to, the gene and promoter chosen, the condition, patient specific parameters, e.g., height, weight and age, and whether prevention or treatment is to be achieved. The vector/device system of the invention is amenable to chronic use for prophylactic or therapeutic purposes.

Vectors of the invention may conveniently be provided in the form of formulations suitable for administration, e.g., into the blood stream (e.g., in an intracoronary artery). A suitable administration format may best be determined by a medical practitioner for each patient individually, according to standard procedures. Suitable pharmaceutically acceptable carriers and their formulation are described in standard formulations treatises, e.g., Remington's Pharmaceuticals Sciences. Vectors of the present invention should preferably be formulated in solution at neutral pH, for example, about pH 6.5 to about pH 8.5, more preferably from about pH 7 to 8, with an excipient to bring the solution to about isotonicity, for example, 4.5% mannitol or 0.9% sodium chloride, pH buffered with art-known buffer solutions, such as sodium phosphate, that are generally regarded as safe, together with an accepted preservative such as metacresol 0.1% to 0.75%, more preferably from 0.15% to 0.4% metacresol. Obtaining a desired isotonicity can be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions. If desired, solutions of the above compositions can also be prepared to enhance shelf life and stability. Therapeutically useful compositions of the invention can be prepared by mixing the ingredients following generally accepted procedures. For example, the selected components can be mixed to produce a concentrated mixture which may then be adjusted to the final concentration and viscosity by the addition of water and/or a buffer to control pH or an additional solute to control tonicity.

The vectors can be provided in a dosage form containing an amount of a vector effective in one or multiple doses. For viral vectors, the effective dose may be in the range of at least about $10^7$ viral particles, preferably about $10^9$ viral particles, and more preferably about $10^{11}$ viral particles. The number of viral particles may, but preferably does not exceed $10^{14}$. As noted, the exact dose to be administered is determined by the attending clinician, but is preferably in 1 ml phosphate buffered saline. For delivery of recombinant cells, the number of cells to be administered will be an amount which results in a beneficial effect to the recipient. For example, from $10^2$ to $10^{10}$, e.g., from $10^3$ to $10^9$, $10^4$ to $10^8$, or $10^5$ to $10^7$, cells can be administered. For delivery of plasmid DNA alone, or plasmid DNA in a complex with other macromolecules, the amount of DNA to be administered will be an amount which results in a beneficial effect to the recipient. For example, from 0.0001 to 1 mg or more, e.g., up to 1 g, in individual or divided doses, e.g., from 0.001 to 0.5 mg, or 0.01 to 0.1 mg, of DNA can be administered.

Administration of the vector in accordance with the present invention may be continuous or intermittent, depending, for example, upon the recipient's physiological condition, whether the purpose of the administration is therapeutic or prophylactic, and other factors known to skilled practitioners. The administration of the gene therapy vector may be essentially continuous over a preselected period of time or may be in a series of spaced doses. Both local and systemic administration is contemplated.

One or more suitable unit dosage forms comprising the vector, which may optionally be formulated for sustained release, can be administered by a variety of routes including oral, or parenteral, including by rectal, buccal, vaginal and sublingual, transdermal, subcutaneous, intravenous, intramuscular, intraperitoneal, intrathoracic, intrapulmonary and intranasal routes. The formulations may, where appropriate, be conveniently presented in discrete unit dosage forms and may be prepared by any of the methods well known to pharmacy. Such methods may include the step of bringing into association the vector with liquid carriers, solid matrices, semi-solid carriers, finely divided solid carriers or combinations thereof, and then, if necessary, introducing or shaping the product into the desired delivery system.

Pharmaceutical formulations containing the vector can be prepared by procedures known in the art using well known and readily available ingredients. For example, the agent can be formulated with common excipients, diluents, or carriers, and formed into tablets, capsules, suspensions, powders, and the like. The vectors of the invention can also be formulated as elixirs or solutions for convenient oral administration or as solutions appropriate for parenteral administration, for instance by intramuscular, subcutaneous or intravenous routes.

The pharmaceutical formulations of the vectors can also take the form of an aqueous or anhydrous solution or dispersion, or alternatively the form of an emulsion or suspension.

Thus, the vector, e.g., in a recombinant virus or genetically modified donor cell, may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the prior art. It is possible, for example, to prepare solutions using one or more organic solvent(s) that is/are acceptable from the physiological standpoint.

For administration to the upper (nasal) or lower respiratory tract by inhalation, the vector is conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatine or blister packs from which the powder may be administered with the aid of an inhalator, insufflator or a metered-dose inhaler.

For intra-nasal administration, the vector may be administered via nose drops, a liquid spray, such as via a plastic bottle atomizer or metered-dose inhaler. Typical of atomizers are the Mistometer (Wintrop) and the Medihaler (Riker).

The local delivery of the vectors can also be by a variety of techniques which administer the vector at or near the site of disease. Examples of site-specific or targeted local delivery techniques are not intended to be limiting but to be illustrative of the techniques available. Examples include local delivery catheters, such as an infusion or indwelling catheter, e.g., a needle infusion catheter, shunts and stents or other implantable devices, site specific carriers, direct injection, or direct applications.

For topical administration, the vectors may be formulated as is known in the art for direct application to a target area. Conventional forms for this purpose include wound dressings, coated bandages or other polymer coverings, ointments, creams, lotions, pastes, jellies, sprays, and aerosols, as well as in toothpaste and mouthwash, or by other suitable forms. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. Nos. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1-25% by weight.

When desired, the above-described formulations can be adapted to give sustained release of the active ingredient employed, e.g., by combination with certain hydrophilic polymer matrices, e.g., comprising natural gels, synthetic polymer gels or mixtures thereof.

Drops, such as eye drops or nose drops, may be formulated with an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle, adapted to deliver liquid contents dropwise, via a specially shaped closure.

The vector may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; mouthwashes comprising the composition of the present invention in a suitable liquid carrier; and pastes and gels, e.g., toothpastes or gels, comprising the composition of the invention.

Additionally, the vectors are well suited to formulation as sustained release dosage forms and the like. The coatings, envelopes, and protective matrices may be made, for example, from polymeric substances, such as polylactideglycolates, liposomes, microemulsions, microparticles, nanoparticles, or waxes.

The formulations and compositions described herein may also contain other ingredients such as antimicrobial agents, or preservatives. Furthermore, as described herein the active ingredients may also be used in combination with other therapeutic agents or therapies.

The formulations and compositions described herein may also contain other ingredients such as antimicrobial agents or preservatives.

Potential Donor Cells and Exemplary Isolation Thereof

A cell population useful in the present invention is one which is capable of developing into cells of mesodermal cell lineage, ectodermal cell lineage and/or endodermal cell lineage. As used herein, mesodermal cells include cells of connective tissue, bone, cartilage, muscle, blood and blood vessel, lymphatic and lymphoid organ, notochord, pleura, pericardium, peritoneum, kidney and gonad. Ectodermal cells include epidermal tissue cells, such as those of nail, hair, glands of the skin, the nervous system, the external sense organs (e.g., eyes and ears) and mucous membranes (such as those of the mouth and anus). Endodermal cells include cells of the epithelium such as those of the pharynx, respiratory tract (except the nose), digestive tract, bladder and urethra cells. In one embodiment, cells within a stem cell population for use in the present invention include cells of at least one of the following cellular lineages: hematopoietic cell lineage, endothelial cell lineage, epithelial cell lineage, muscle cell lineage and/or neural cell lineage or having the potential to differentiate into one or more of these lineages.

A variety of stem and progenitor cell populations may be used. Each cell type has its own profile of advantages. For instance, unfractionated bone marrow cells (BMCs) contain different stem and progenitor cell populations, including HSCs, endothelial progenitor cells (EPCs), and mesenchymal stem cells (MSCs). Ease of harvest and lack of extensive requirement for ex vivo manipulation are advantages of using unselected BMCs.

EPCs were originally defined by their cell surface expression of the hematopoietic marker proteins CD133 and CD34 and the endothelial marker vascular endothelial growth factor receptor-2, and their capacity to incorporate into sites of neovascularization and to differentiate into endothelial cells in situ (Asahara, *Am. J. Physiol. Cell Physiol.*, 287:C572 (2004)). Increasing evidence suggests that culture-expanded EPCs also contain a $CD14^+/CD34^-$-mononuclear cell population with "EPC capacity," which mediates its angiogenic effects by releasing paracrine factors (Rehman et al., *Circulation*, 107:1165 (2003); Urbich et al., *Circ. Res.*, 95:343 (2004)).

The cell surface antigen CD133 is expressed on early HSCs and EPCs, both of which collaborate to promote vascularization of ischemic tissues (Rafii et al., *Nat. Med.*, 9:702 (2003)). $CD133^+$ cells can integrate into sites of neovascularization and differentiate into mature endothelial cells. Because CD133 expression is lost on myelomonocytic cells, this marker provides an effective means to distinguish "true" $CD133^+$ EPCs from EPCs of myelomonocytic origin (Rehman et al., supra). Less than 1% of nucleated BMCs are $CD133^+$, and because these cells cannot be expanded ex vivo, only limited numbers of $CD133^+$ cells can be obtained for therapeutic purposes.

MSCs represent a rare population of $CD34^-$ and $CD133^-$ cells present in bone marrow stroma (10-fold less abundant than HSCs) and other mesenchymal tissues (Pittenger et al., *Circ. Res.*, 95:9 (2004)). MSCs can readily differentiate into osteocytes, chondrocytes, and adipocytes. Differentiation of MSCs to cardiomyocyte-like cells has been observed under specific culture conditions and after injection into healthy or infarcted myocardium in animals (Makino et al., *J. Clin. Invest.*, 103:697 (1999); Toma et al., *Circulation*, 105:93 (2002); Mangi et al., *Nat. Med.*, 9:1195 (2003)). When injected into infarct tissue, MSCs may enhance regional wall motion and prevent remodeling of the remote, non-infarcted myocardium (Mangi et al., 2003; Shake et al., *Ann. Thorac. Surg.*, 73:1919 (2002). Cultured MSCs secrete angiogenic cytokines, which improve collateral blood flow recovery in a murine hind limb ischemia model (Kinnaird et al., *Circ. Res.*, 94:678 (2004)). Because MSC clones can be expanded in vitro, and reportedly have a low immunogenicity, they may be used in an allogeneic setting (Pittenger et al., *Circ. Res.*, 95:9 (2004)).

Skeletal myoblasts, or satellite cells, are progenitor cells that normally lie in a quiescent state under the basal membrane of mature muscular fibers. Myoblasts can be isolated from skeletal muscle biopsies and expanded in vitro. Myoblasts differentiate into myotubes and retain skeletal muscle properties when transplanted into an infarct scar (Ghostine et al., *Circulation*, 106:I131 (2002); Murry et al., *J. Clin. Invest.*, 98:2512 (1996); Leobon et al., *Proc. Natl. Acad. Sci. USA*, 100:7808 (2003); Pagani et al., *J. Am. Coll. Cardiol.*, 41:879 (2003)). Myoblast transplantation has been shown to augment systolic and diastolic performance in animal models of myocardial infarction (Dowell et al., *Cardiovasc. Res.*, 58:336 (2003)).

Adult cardiac uncommitted progenitor cells (UPCs; see Ott et al., *Nat. Clin. Pract. Cardiovasc. Med.*, S1:S27 (2007); WO 07/024,036; U.S. application Publication No. 2006512009; WO 05/KR/2834) and resident cardiac stem cell (CSC) population(s) are capable of differentiating into cardiomyocyte or vascular lineages (Hierlihy et al., *FEBS Lett.*, 530:239 (2002); Beltrami et al., *Cell*, 114:763 (2003); Oh et al., *Proc. Natl. Acad. Sci. USA*, 100:12313 (2003); Martin et al., *Dev. Biol.*, 265:262 (2004); Messina et al., *Circ. Res.*, 95:911 (2004)). Intriguingly, CSCs can be clonally expand from human myocardial biopsies (Messina et al., 2004). It has been reported that intramyocardial injection of these cells after AMI in mice promotes cardiomyocyte and vascular cell formation and leads to an improvement in systolic function (Messina et al., 2004).

Embryonic stem (ES) cells are totipotent stem cells derived from the inner cell mass of blastocysts. Under specific culture conditions, ES cells differentiate into multicellular embryoid bodies containing differentiated cells from all three germ layers including cardiomyocytes. Human ES cell-derived cardiomyocytes display structural and functional properties of early-stage cardiomyocytes that couple electrically with host cardiomyocytes when transplanted into normal myocardium (Kehat et al., *J. Clin. Invest.*, 108:407 (2001); Kehat et al., *Nat. Biotechnol.*, 22:1282 (2004)). Nuclear transfer techniques provide a means for generating an unlimited supply of histocompatible ES cells for the treatment of cardiac disease (therapeutic cloning) (Lanza et al., *Circ. Res.*, 94:820 (2004)).

Donor cells within the scope of the invention include but are not limited to bone marrow-derived cells, e.g., mesenchymal cells and stromal cells, smooth muscle cells, fibroblasts, SP cells, pluripotent cells or totipotent cells, e.g., teratoma cells, hematopoietic stem cells, for instance, cells from cord blood and isolated CD34+cells, multipotent adult progenitor cells, adult stem cells, embryonic stem cells, skeletal muscle derived cells, for instance, skeletal muscle cells and skeletal myoblasts, cardiac derived cells, myocytes, e.g., ventricular myocytes, atrial myocytes, SA nodal myocytes, AV nodal myocytes, and Purkinje cells. The term "donor cell" includes embryonic, fetal, pediatric, or adult cells or tissues, including but not limited to, stem cells and precursors (progenitor) cells. Thus, donor cells of the invention can be myocardial cells, bone marrow cells, hematopoietic cells, lymphocytes, leukocytes, granulocytes, hepatocytes, monocytes, macrophages, fibroblasts, neural cells, mesenchymal stem cells, beta-islet cells, and combinations thereof, or cells capable of differentiating into those cells. In one embodiment, the donor cells are autologous cells, however, non-autologous cells, e.g., xenogeneic cells, may also be employed. In one embodiment, the donor cells are endothelial progenitor cells, CD133+cells, CD34+cells, mesenchymal stem cells, skeletal myoblasts, neural stem cells, pancreatic beta cells, cardiac stem cells or embryonic stem cells.

Stem cells may be isolated from any source known in the art and includes, but is not limited to, e.g., peripheral blood stem cells (PBSC), stem cells isolated from bone marrow; stem cells isolated from adipose tissue; mesenchymal stem cells, embryonic stem cells, CD34+ cells, CD34− cells, CD45+ cells, or combinations thereof). Stem cells which express one or more of the following antigens may be useful in the methods of the invention: CD34, CD133, ABCG2, Sca-1, Stro-1, nestin, PSA-NCAm, P75 neurotrophin, c-kit or CD30. Exemplary stem cells and methods of isolating them are described in, e.g., Fickert et al., *Osteoarthritis Cartilage*, 11:790 (2003), which discloses identification, quantification and isolation of human mesenchymal progenitor cells from osteoarthritic synovium; Meirelles et al., *Br. J. Haematol.*, 123:702 (2003), which discloses isolation, in vitro expansion, and characterization of mesenchymal stem cell from bone marrow; Pittenger et al., *Science*, 284:143 (1999), which discloses isolation, analysis, and differentiation of adult human mesenchymal stem cells from bone marrow; Lataillade et al., *Blood*, 95:756 (2000) or Handgretinger et al., *Bone Marrow Transplant*, 27:777 (2001), which disclose isolation, analysis, and purification of adult human peripheral blood CD34+ progenitor cells; U.S. Pat. No. 6,667,034 which discloses isolation and differentiation of stem cells from human hematopoietic cells, i.e., from bone marrow and peripheral blood; and U.S. Pat. No. 6,261,549 which discloses isolation of human mesenchymal stem cells from peripheral blood; and Gepstein, *Circ. Res.*, 91:866 (2002), which discloses derivation of embryonic stem cells.

Typically, stem cells are purified from peripheral blood using methods known in the art including, e.g., immunomagnetic selection with the MACS system (Miltenyi Biotech, Tebu) or antibody-coated Dynabeads (Dynal Biotech, Oslo). A heterogenous population of cells may be contacted with antibody-coated magnetic beads. The antibody specifically binds to a cell surface marker differentially or preferentially expressed on the surface of a stem cell, thereby forming a complex between the beads and the stem cells in the heterogenous population. The labeled stem cells can then be isolated from the heterogenous cell population using methods known in the art including, e.g., flow cytometry.

For example, bone marrow is aspirated from the posterior iliac crest under a brief general anesthesia. Unselected BMCs are enriched under good manufacturing practice conditions by 4% gelatin-polysuccinate density gradient sedimentation as described in Wollert et al. (*Lancet*, 364:141 (2004)). CD34+cells may be immunomagnetically enriched from unselected BMCs by the CliniMACS$^{plus}$ System and CD34 antibodies from Miltenyi Biotech. The number of CD34+cells in unselected BMC preparations and in CD34-enriched preparations may be determined by flow cytometry analysis (FACSCalibur, BD Biosciences) using an antibody from Beckman Coulter.

Alternatively, BMCs are isolated by Ficoll density gradient centrifugation. After two washing steps, cells are resuspended to yield a heterogeneous cell population including hematopoietic progenitor cells, but also other cell types (e.g., side population cells, stromal cells, and so on). Overall, a mean value of $5.5 \pm 3.9 \times 10^6$ CD34/CD45-positive cells may be infused per patient.

For CPCs, mononuclear cells from venous blood are suspended in medium supplemented with 1 ng/ml carrier-free human recombinant vascular endothelial growth factor (R&D, Wiesbaden, Germany), 0.1 µmol/L atorvastatin (Pfizer, Freiburg, Germany), and 20% human serum drawn from each individual patient. Cells are seeded at a density of $6.4 \times 10^5$ cells/mm$^2$ on fibronectin-coated dishes (Roche, Grenzach, Germany). After three days of cultivation, cells are detached with 0.5 mmol/L ethylenediamine-tetraacetic acid, washed twice, and re-suspended in a final volume of 10 ml of medium. The resulting cell suspension contains a heterogeneous population of progenitor cells, however, more than 90% of the cells show endothelial characteristics, as demonstrated by Dil-acetylated low-density lipoprotein-uptake and lectin binding and the expression of typical endothelial marker proteins including vascular endothelial growth factor-R2 (KDR) (ReliaTech, Braunschweig, Germany), endoglin (CD105) (NeoMarkers, Asbach, Germany), von Willebrand factor (Oncogene, Schwalbach, Germany), and platelet endothelial cell adhesion molecule-1 (PECAM-1/CD31) (Dianova, Hamburg, Germany) (Assmus et al., *Circulation*, 106: 3009 (2002); Dimmeler et al., *J. Clin. Invest.*, 108:391 (2001); Vasa et al., *Circulation*, 103:2885 (2001); Vasa et al., *Circ. Res.*, 89:1 (2001)).

Various techniques may be employed to separate the cells by initially removing cells of dedicated lineage. Monoclonal antibodies are particularly useful for identifying markers associated with particular cell lineages and/or stages of differentiation.

If desired, a large proportion of terminally differentiated cells may be removed by initially using a "relatively crude" separation. For example, magnetic bead separations may be used initially to remove large numbers of lineage committed cells. Desirably, at least about 80%, usually at least 70% of the total hematopoietic cells are removed.

Procedures for separation may include but are not limited to, magnetic separation, using antibody-coated magnetic beads, affinity chromatography, cytotoxic agents joined to a monoclonal antibody or used in conjunction with a monoclonal antibody, including but not limited to, complement and cytotoxins, and "panning" with antibody attached to a solid matrix, e.g., plate, elutriation or any other convenient technique.

Techniques providing accurate separation include but are not limited to, flow cytometry, which can have varying degrees of sophistication, e.g., a plurality of color channels, low angle and obtuse light scattering detecting channels, impedance channels, etc.

Donor cells can be expanded in vitro to provide an expanded population of donor cells for administration. In addition, donor cells may be treated in vitro (ex vivo) to induce certain phenotypic characteristics, e.g., to induce proliferation or differentiation. Thus, donor cells may be primed or preconditioned, e.g., treated with a cytokine or a mixture of cytokines.

Delivery of exogenous transgenes may be accomplished by any means, e.g., transfection with naked DNA, e.g., a vector comprising the transgene, liposomes, calcium-mediated transformation, electroporation, or transduction, e.g., using recombinant viruses. A number of transfection techniques are generally known in the art. See, e.g., Graham et al., *Virology*, 52, 456 (1973), Sambrook et al., *Molecular Cloning: A Laboratory Manual*, Cold Spring Harbor Laboratories, New York (1989), Davis et al., *Basic Methods in Molecular Biology*, Elsevier (1986) and Chu et al., *Gene*, 13, 197 (1981). Particularly suitable transfection methods include calcium phosphate co-precipitation (Graham et al., *Virol.*, 52, 456 (1973)), direct microinjection into cultured cells (Capecchi, *Cell*, 22, 479 (1980)), electroporation (Shigekawa et al., *BioTechniques*, 6, 742 (1988)), liposome-mediated gene transfer (Mannino et al., *BioTechniques*, 6, 682 (1988)), lipid-mediated transduction (Felgner et al., *Proc. Natl. Acad. Sci. USA*, 84, 7413 (1987)), and nucleic acid delivery using high-velocity microprojectiles (Klein et al., *Nature*, 327, 70 (1987)). Gene delivery vectors include, but are not limited to, isolated nucleic acid, e.g., plasmid-based vectors which may be extra-chromosomally maintained, and viral vectors, e.g., recombinant adenovirus, retrovirus, lentivirus, herpesvirus including cytomegalovirus, poxvirus, papilloma virus, or adeno-associated virus, including viral and non-viral vectors which are present in liposomes, e.g., neutral or cationic liposomes, such as DOSPA/DOPE, DOGS/DOPE or DMRIE/DOPE liposomes, and/or associated with other molecules such as DNA-anti-DNA antibody-cationic lipid (DOTMA/DOPE) complexes.

Devices

FIGS. 7-13 illustrate an optical depolarizing system (ODS) as part of a cardiac rhythm management (CRM) system. While an implantable medical device of a CRM system is discussed as a specific example illustrating an apparatus for emitting light inconjunction with the vector discussed above, the present ODS generally applies to depolarization of any optically excitable tissue using any light emitting device configured to emit a light having suitable characteristics. For example, a light emitting device may be incorporated into a percutaneous transluminal catheter for applying light to myocardial tissue. In another example, the light is applied to a portion of the nervous system for neural activation. Generally, the light is applied to treat a wide range of channelopathies in tissues or organs such as the heart, skeletal muscle, smooth muscle, kidney, ear, pancreas, and nerves.

As used in this document, the relationship between a heart rate and a cardiac cycle length (also known as cardiac interval) is the relationship between a frequency and its corresponding period. If a heart rate is given in beats per minute (bpm), its corresponding cardiac cycle length in milliseconds is calculated by dividing 60,000 by the heart rate (where 60,000 is the number of milliseconds in a minute). Any process, such as a comparison, using a heart rate is to be modified accordingly when a cardiac cycle length is used instead. For example, if a tachyarrhythmia is detected when the ventricular rate exceeds a tachyarrhythmia threshold rate, an equivalent process is to detect the tachyarrhythmia when the ventricular cycle length (also known as ventricular interval) falls below a tachyarrhythmia threshold interval. The appended claims should be construed to cover such variations.

In this document, a "fast beat" refers to a heart beat having a heart rate that falls into a tachyarrhythmia detection zone, which is typically defined by at least one tachyarrhythmia detection threshold, and a "slow beat" refers to a heart beat having a heart rate that is below the tachyarrhythmia detection zone. In other words, a "fast beat" is a heart beat having a tachyarrhythmic heart rate, and a "slow beat" is a heart beat having a heart rate that is not tachyarrhythmic.

Figure 7:
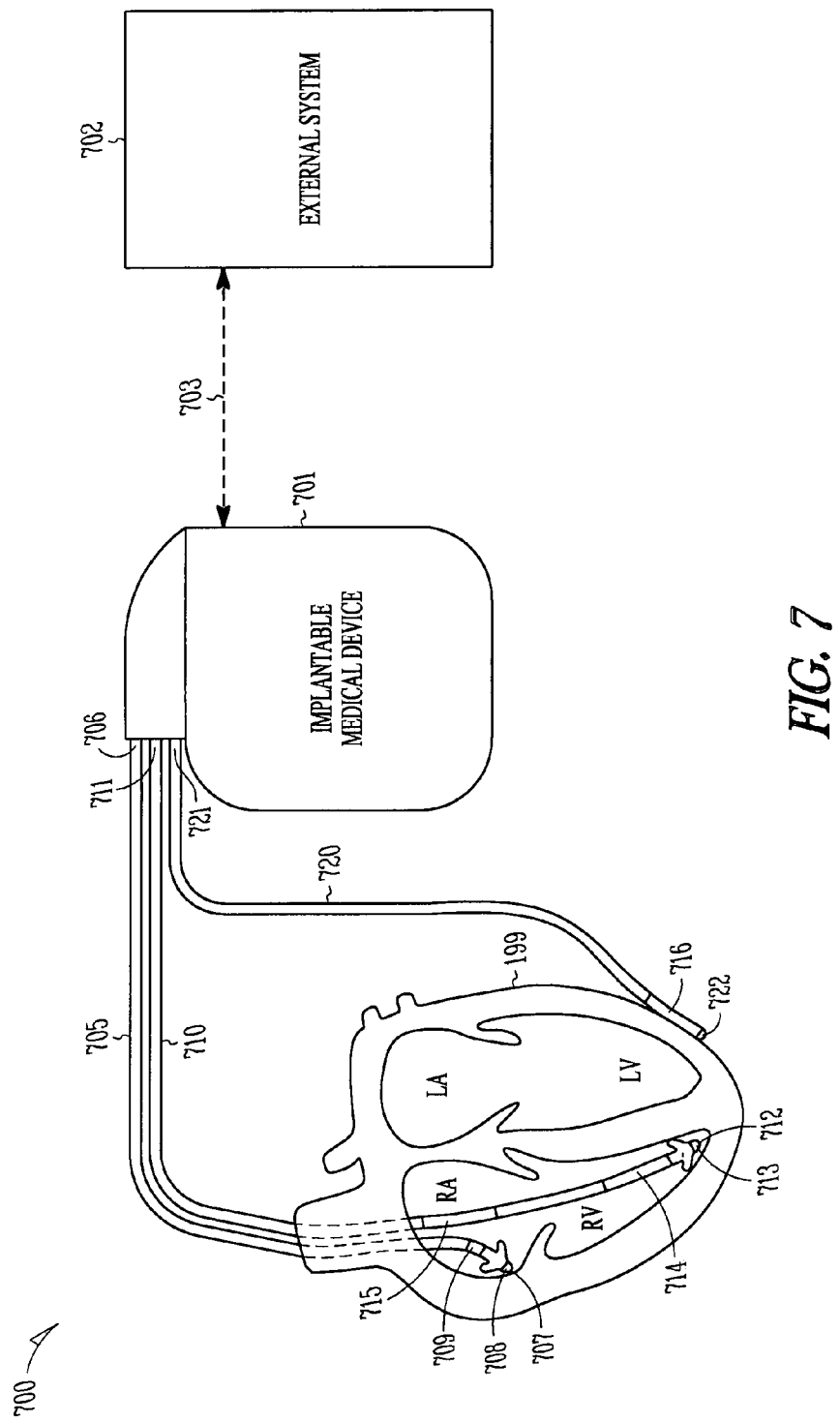
FIG. 7 is an illustration of an embodiment of a cardiac rhythm management (CRM) system and portions of the environment in which the CRM system operates.

FIG. 7 is an illustration of an embodiment of a CRM system 700 and portions of the environment in which CRM system 700 operates. CRM system 700 includes an implantable medical device 701 that is coupled to a heart 199 through leads 705 and 710. An external system 702 communicates with implantable medical device 701 via a telemetry link 703.

Implantable medical device 701 includes a hermetically sealed can housing an electronic circuit that senses physiological signals and delivers one or more cardiac therapies including a light therapy for depolarizing myocardial tissue of heart 199 using optical energy. The hermetically sealed can may also function as an electrode for sensing and/or therapy delivery purposes. In one embodiment, as illustrated in FIG. 7, the electronic circuit senses at least an atrial electrogram and a ventricular electrogram from heart 199 and delivers at least an optical defibrillation therapy to heart 199. In the illustrated embodiment, lead 705 is an endocardial pacing lead that includes a proximal end 706 connected to implantable medical device 701 and a distal end 707 placed in the right atrium (RA) of heart 199. A pacing-sensing electrode 708 is located at distal end 707. Another pacing-sensing electrode 709 is located near distal end 707. Electrodes 708 and 709 are electronically connected to implantable medical device 701 via separate conductors in lead 705 to allow for sensing of the atrial electrogram and/or delivery of electrical atrial pacing pulses. Lead 710 is an endocardial defibrillation lead that includes a proximal end 711 connected to implantable medical device 701 and a distal end 712 placed in the right ventricle (RV) of heart 199. A pacing-sensing electrode 713 is located at distal end 712 and electrically connected to implantable medical device 710 via a conductor in lead 710. A light emission device 714 is incorporated into a portion of lead 710 for endocardial placement in the RV. Another light emission device 715 is incorporated into another portion of lead 710 for endocardial placement in the RA. Electrode 113 allows for sensing of the ventricular electrogram and/or delivery of electrical ventricular pacing pulses. Light emission device 714 provides for ventricular defibrillation by optically depolarizing portions of myocardial tissue of the RV. Light emission device 715 provides for atrial defibrillation by optically depolarizing portions of myocardial tissue of the RA. Lead 720 is an epicardial defibrillation lead that includes a proximal end 721 connected to implantable medical device 701 and a distal end 722 placed on heart 199 over the left ventricle (LV). A light emission device 716 is incorporated into a portion of lead 720 for epicardial placement over the LV, to provide for ventricular defibrillation by optically depolarizing portions of myocardial tissue of the LV. The configuration and functions of these leads are discussed above by way of example and not by way of limitation. Other ways of configuring such leads, including electrodes and/or light emission devices, are applied as determined based on a patient's specific condition and/or specific therapy algorithms.

Implantable medical device 701 and/or external system 702 control the emission of the light from one or more of light emission devices 714, 715, and 716. In one embodiment, implantable medical device 701 detects and classifies tachyarrhythmias and controls the emission of the light in response to the detection of a tachyarrhythmia episode that is classified as a type for which light therapy is available for delivery using CRM system 700. In another embodiment, the light is delivered in response to a command received from external system 702 via telemetry link 703. In one embodiment, in addition to the optical defibrillation, implantable medical device 701 provides for optical cardiac pacing, electrical cardiac pacing, and/or electrical defibrillation.

External system 702 allows for programming of implantable medical device 701 and receives signals acquired by implantable medical device 701. In one embodiment, external system 702 includes a programmer. In another embodiment, external system 702 is a patient management system including an external device in proximity of implantable medical device 701, a remote device in a relatively distant location, and a telecommunication network linking the external device and the remote device. The patient management system provides for access to implantable medical device 701 from a remote location, such as for monitoring patient status and/or adjusting therapies. In one embodiment, telemetry link 703 is an inductive telemetry link. In an alternative embodiment, telemetry link 703 is a far-field radio-frequency telemetry link. Telemetry link 703 provides for data transmission from implantable medical device 701 to external system 702. This may include, for example, transmitting real-time physiological data acquired by implantable medical device 701, extracting physiological data acquired by and stored in implantable medical device 701, extracting therapy history data stored in implantable medical device 701, and extracting data indicating an operational status of implantable medical device 701 (e.g., battery status and lead impedance). Telemetry link 703 also provides for data transmission from external system 702 to implantable medical device 701. This may include, for example, programming implantable medical device 701 to acquire physiological data, programming implantable medical device 701 to perform at least one self-diagnostic test (such as for a device operational status), programming implantable medical device 701 to deliver a defibrillation therapy such as the light therapy.

The circuit of implantable medical device 701, including its various elements discussed in this document, may be implemented using a combination of hardware and software. In various embodiments, each element of implantable medical device 701 discussed in this document may be implemented using an application specific circuit constructed to perform one or more particular functions or a general purpose circuit programmed to perform such function(s). Such a general purpose circuit includes, but is not limited to, a microprocessor or a portion thereof, a microcontroller or portions thereof, and a programmable logic circuit or a portion thereof. For example, a "comparator" includes, among other things, an electronic circuit comparator constructed to perform the only function of a comparison between two signals or a portion of a general-purpose circuit driven by a code instructing that portion of the general purpose circuit to perform the comparison between the two signals.

Figure 8:
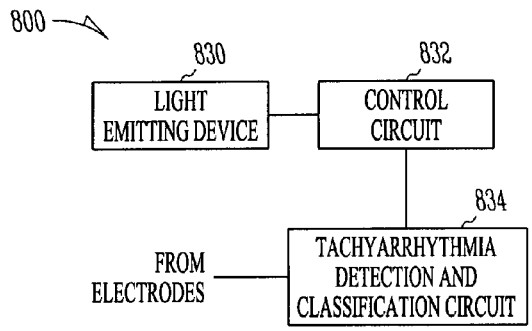
FIG. 8 is a block diagram illustrating an embodiment of an ODS of the CRM system.

FIG. 8 is a block diagram illustrating an embodiment of an ODS 800 of CRM system 700. ODS 800 includes a light emitting device 830, a control circuit 832, and a tachyarrhythmia detection and classification circuit 834.

Light emitting device 830 represents light emission devices 714, 715, and/or 716. In one embodiment, light emitting device 830 includes one or more light sources each configured to deliver a light having specified frequency characteristics suitable for optically depolarizing cardiac tissue. In one embodiment, the light has a wavelength between 340 and 700 nanometers, with 470 nanometers being a specific embodiment. In one embodiment, the light includes blue light. Light emitting device 830 is placed in close proximity to the genetically altered cells, e.g., epicardially, as blue light does not penetrate as deeply as, for instance, red light. For example, to treat AF, a vector encoding a light sensitive protein which is sensitive to blue light is administered epicardially or systemically, and light emitting device 830, which emits the blue light, is placed epicardially over an atrium. In another embodiment, the light includes a red light. For example, to treat AF, a vector encoding a light sensitive protein which is sensitive to red light is administered, and light emitting device 830, which emits red light, is placed epicardially or in a blood vessel over an atrium.

Control circuit 832 controls the emission of light from light emitting device 830. In one embodiment, control circuit 832 initiates, adjusts, and/or stops the emission of light in response to a detection and classification of tachyarrhythmia by tachyarrhythmia detection and classification circuit 834.

Tachyarrhythmia detection and classification circuit 834 detects and classifies tachyarrhythmia episode using at least one or more cardiac signals sensed using electrodes such as those illustrated in FIG. 7. In one embodiment, in addition to one or more cardiac signals, tachyarrhythmia detection and classification circuit 834 uses one or more other physiological signals, such as one or more signals indicative of hemodynamic performance, to detect and classify tachyarrhythmia episode.

Figure 9:
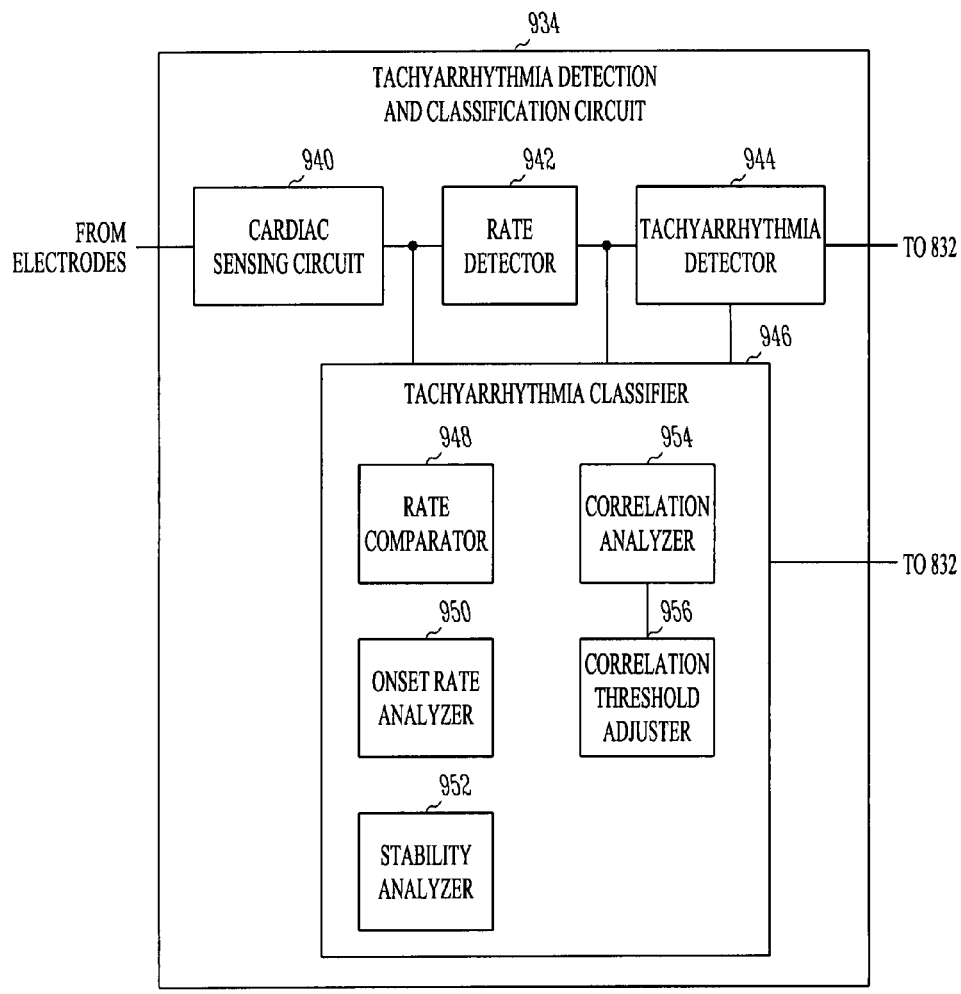
FIG. 9 is a block diagram illustrating an embodiment of a tachyarrhythmia detection and classification circuit of the ICD.

FIG. 9 is a block diagram illustrating an embodiment of a tachyarrhythmia detection and classification circuit 934. Tachyarrhythmia detection and classification circuit 934 is a specific embodiment of tachyarrhythmia detection and classification circuit 834 and includes a cardiac sensing circuit 940, a rate detector 942, a tachyarrhythmia detector 944, and a tachyarrhythmia classifier 946.

Cardiac sensing circuit 940 senses one or more cardiac signals, such as one or more electrograms, using electrodes such as those illustrated in FIG. 7. In one embodiment, cardiac sensing circuit 940 is electrically coupled to heart 199 through leads 705 and 710 to sense an atrial electrogram and a ventricular electrogram from the heart. The atrial electrogram includes atrial events, also known as P waves, each indicative of an atrial depolarization. The ventricular electrogram includes ventricular events, also known as R waves, each indicative of a ventricular depolarization.

Rate detector 942 detects one or more heart rates from one or more cardiac signals sensed by cardiac sensing circuit 940. In one embodiment, rate detector 942 detects an atrial rate from the atrial electrogram and a ventricular rate from the ventricular electrogram. The atrial rate is the frequency of the atrial events. The ventricular rate is the frequency of the ventricular events. In one embodiment, the atrial and ventricular rates are each expressed in beats per minute (bpm), i.e., number of detected atrial or ventricular depolarizations per minute.

Tachyarrhythmia detector 944 detects a tachyarrhythmia episode. In one embodiment, a tachyarrhythmia is detected when the ventricular rate exceeds a predetermined tachyarrhythmia threshold rate. In one embodiment, tachyarrhythmia detector 944 detects tachyarrhythmia by determining whether the ventricular rate is within one of a plurality of tachyarrhythmia rate zones each including a predetermined threshold rate. In a specific embodiment, the plurality of tachyarrhythmia rate zones includes a ventricular fibrillation (VF) rate zone with a VF threshold rate programmable between 130 and 250 bpm, a fast ventricular tachycardia (VT) rate zone with a fast VT threshold rate programmable between 110 and 210 bpm, and a slow VT rate zone with a slow VT threshold rate programmable between 90 and 200 bpm. In another embodiment, the tachyarrhythmia is detected using a "zoneless tachyarrhythmia detection" method, as discussed in U.S. patent application Ser. No. 11/301,716, "ZONELESS TACHYARRHYTHMIA DETECTION WITH REAL-TIME RHYTHM MONITORING", filed on Dec. 13, 2005, assigned to Cardiac Pacemakers, Inc., which is incorporated herein by reference in its entirety.

Tachyarrhythmia classifier 946 classifies each tachyarrhythmia detected by tachyarrhythmia detector 944. Examples of classification of tachyarrhythmia made by tachyarrhythmia classifier 946 include ventricular fibrillation (VF), ventricular tachycardia (VT), supraventricular tachyarrhythmia (SVT), atrial fibrillation (AF), atrial flutter (AFL), sinus tachycardia (ST), and atrial tachycardia (AT). In one embodiment, a detected tachyarrhythmia is classified as VF when the ventricular rate falls within the VF rate zone, without further analysis by tachyarrhythmia classifier 346. In the illustrated embodiment, tachyarrhythmia classifier 946 includes a rate comparator 948, an onset rate analyzer 950, a stability analyzer 952, a correlation analyzer 954, and a correlation threshold adjuster 956. Rate comparator 948 compares the atrial rate and the ventricular rate to determine whether the atrial rate exceeds, equals, or is lower than the ventricular rate by a predetermined margin. Onset rate analyzer 950 produces an onset rate of the detected tachyarrhythmia and determines whether the detected tachyarrhythmia has a gradual onset or a sudden onset by comparing the onset rate to one or more threshold onset rates. The onset rate is a rate of transition of the ventricular rate from a normal sinus rate to a tachyarrhythmic rate when the detected tachyarrhythmia begins. A gradual onset typically indicates a physiological tachyarrhythmia, such as an ST caused by exercise. A sudden onset typically indicates a pathological tachyarrhythmia. Stability analyzer 952 produces a stability parameter indicative of a degree of ventricular rate variability and determines whether the ventricular rate is stable by comparing the stability parameter to a stability threshold. In one embodiment, the stability parameter is produced as an average variance of a series of ventricular intervals. Correlation analyzer 954 analyzes a correlation between a tachyarrhythmic waveform and a template waveform and produces a correlation, coefficient representative of that correlation. The tachyarrhythmic waveform includes a segment of a cardiac signal sensed during the detected tachyarrhythmia. The template waveform is recorded during a known cardiac rhythm such as the normal sinus rhythm (NSR). One example for producing such a correlation coefficient, referred to as a feature correlation coefficient (FCC), is discussed in U.S. Pat. No. 6,708,058, "NORMAL CARDIAC RHYTHM TEMPLATE GENERATION SYSTEM AND METHOD," assigned to Cardiac Pacemakers, Inc., which is hereby incorporated in its entirety. In one embodiment, the detected tachyarrhythmia is considered as "correlated" if a correlation coefficient exceeds a correlation threshold and as "marginally correlated" if the correlation coefficient exceeds a marginal correlation threshold that is lower than the correlation threshold. Correlation threshold adjuster 956 allows adjustment of the marginal correlation threshold. Tachyarrhythmia classifier 946 classifies the detected tachyarrhythmia using one or more of the atrial rate, ventricular rate, onset rate, stability parameter, and correlation coefficient. In one embodiment, tachyarrhythmia classifier 946 classifies the detected tachyarrhythmia using a method discussed below with reference to FIG. 10.

In one embodiment, tachyarrhythmia detector 944 performs a detection process that is initiated by a detection of three consecutive fast beats from the ventricular electrogram. In response to the detection of three consecutive fast beats, a tachyarrhythmia detection window is started. The tachyarrhythmia detection window includes ten consecutively detected heart beats starting with and including the three consecutive fast beats. If at least eight out of the ten heart beats in the tachyarrhythmia detection window are fast beats (i.e., the tachyarrhythmia detection window is satisfied), a tachyarrhythmia verification duration is started. Otherwise, the tachyarrhythmia verification duration is not started.

During the tachyarrhythmia verification duration, a moving verification window of ten consecutively detected heart beats is used to determine whether the detected tachyarrhythmia sustains. If at least six out of the ten heart beats in the verification window are fast beats (i.e., the verification window is satisfied), the detected tachyarrhythmia is considered to be sustaining. If this verification window fails to be satisfied at any time during the tachyarrhythmia verification duration, the tachyarrhythmia detection is terminated without delivering an anti-tachyarrhythmia therapy. If the detected tachyarrhythmia episode is determined to be sustaining throughout the tachyarrhythmia verification duration, it is classified by tachyarrhythmia classifier 946 to determine the necessity and type of an anti-tachyarrhythmia therapy. If the detected tachyarrhythmia is classified as a type of tachyarrhythmia for which a defibrillation therapy is to be delivered, such as a VT or VF, an optical defibrillation therapy is delivered. Following the delivery of the optical defibrillation therapy, the tachyarrhythmia is redetected by repeating the detection and classification process or portions thereof.

Figure 10:
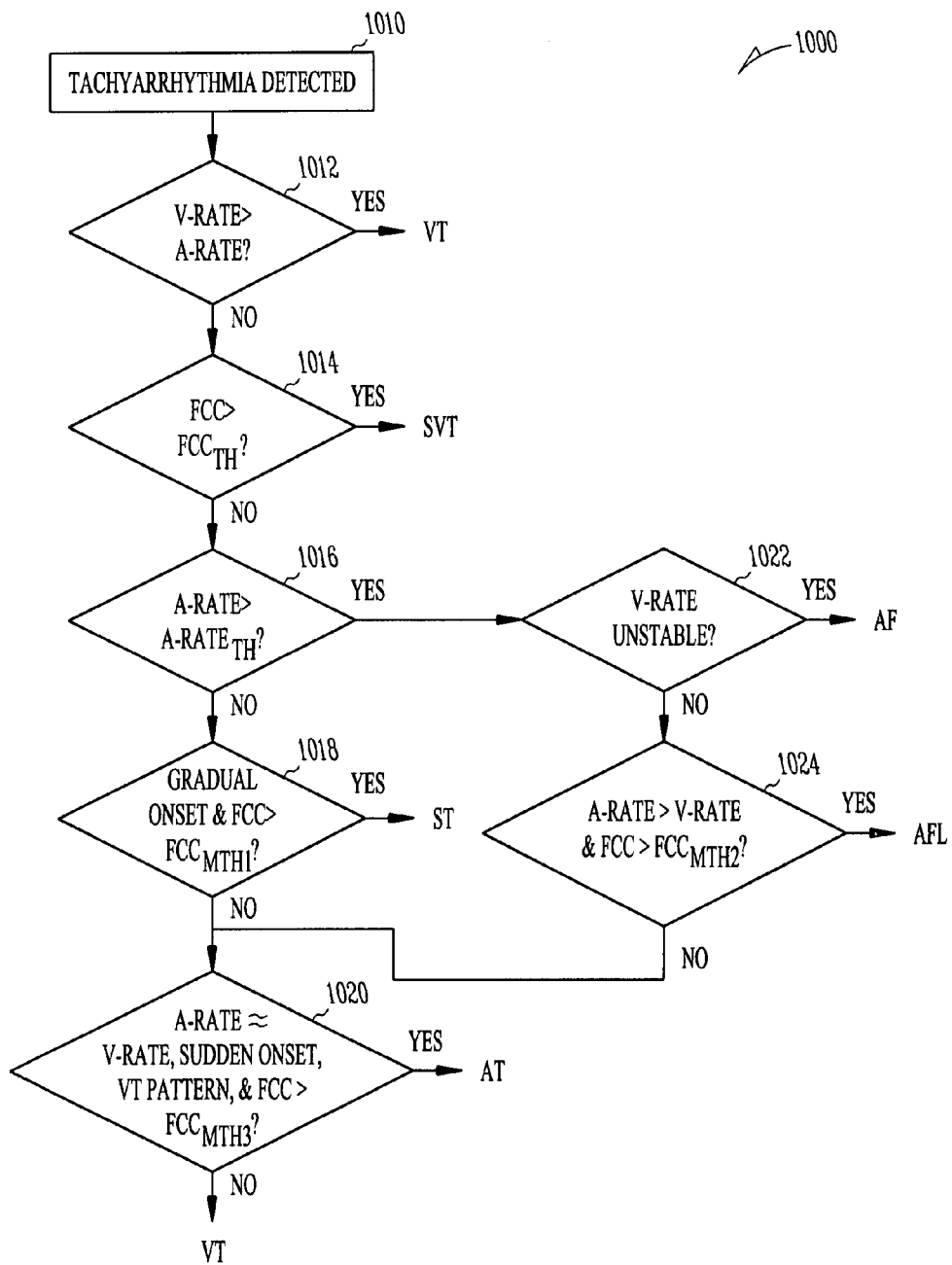
FIG. 10 is a flow chart illustrating an embodiment of a method for classifying detected tachyarrhythmia.

FIG. 10 is a flow chart illustrating a method 1000 for classifying a detected tachyarrhythmia. In one embodiment, tachyarrhythmia classifier 946 performs method 1000. The atrial rate, ventricular rate, onset rate, stability parameter, correlation coefficient, and various thresholds used in method 1000 are detected, produced, or programmed as discussed with reference to FIG. 9 above. For correlation analysis, the template waveform is produced using a cardiac signal sensed during an NSR.

A tachyarrhythmia is detected at 1010, when the ventricular rate is within a predetermined tachyarrhythmia rate zone. If the ventricular rate (V-RATE) exceeds the atrial rate (A-RATE) by a predetermined margin at 1012, the detected tachyarrhythmia is classified as VT. If the ventricular rate does not exceed the atrial rate by a predetermined margin at 1012, and the correlation coefficient (FCC) exceeds the correlation threshold ($FCC_{TH}$) at 1014, the detected tachyarrhythmia is classified as SVT. In one embodiment, the correlation threshold ($FCC_{TH}$) is programmable between 0.6 and 0.99, with approximately 0.94 being a specific example.

If the atrial rate does not exceed a predetermined threshold atrial rate ($A-RATE_{TH}$) at 1016, the onset rate indicates a gradual onset of tachyarrhythmia at 1018, and the correlation coefficient exceeds a first marginal correlation threshold ($FCC_{MTH1}$) (i.e., FCC falls between $FCC_{MTH1}$ and $FCC_{TH}$) at 1018, the detected tachyarrhythmia is classified as ST. ST is a physiologic tachyarrhythmia originated in an SA node when the SA node generates the electrical impulses at a tachyarrhythmic rate. In one embodiment, the first marginal correlation coefficient is programmable between 0.4 and the correlation threshold (i.e., $0.4 \leq FCC_{MTH1} \leq FCC_{TH}$), with approximately 0.8 being a specific example. In one embodiment, the first marginal correlation threshold is set to be lower than the correlation threshold by a predetermined amount, such as approximately 0.2 (i.e., $FCC_{MTH1} \approx FCC_{TH} - 0.2$).

If the correlation coefficient does not exceed the correlation threshold at 1014, the atrial rate exceeds a predetermined threshold atrial rate at 1016, and the ventricular rate is unstable at 1022, the detected tachyarrhythmia is classified as AF. If the ventricular rate is stable at 1022, the atrial rate exceeds the ventricular rate by a predetermined margin, and the correlation coefficient exceeds a second marginal correlation threshold ($FCC_{MTH2}$) (i.e., FCC falls between $FCC_{MTH2}$ and $FCC_{TH}$) at 1024, the detected tachyarrhythmia is classified as AFL. In one embodiment, the second marginal correlation threshold is programmable between 0.4 and the correlation threshold (i.e., $0.4 \leq FCC_{MTH2} \leq FCC_{TH}$), with approximately 0.8 being a specific example. In one embodiment, the second marginal correlation threshold is set to be lower than the correlation threshold by a predetermined amount, such as approximately 0.2 (i.e., $FCC_{MTH2} \approx FCC_{TH} - 0.2$).

If the atrial rate approximately equals to the ventricular rate at 1020, the onset rate indicates a sudden onset of tachyarrhythmia, the atrial and ventricular events occur in a specified SVT pattern, and the correlation coefficient exceeds a third marginal correlation threshold ($FCC_{MTH3}$) (i.e., FCC falls between $FCC_{MTH3}$ and $FCC_{TH}$) at 1020, the detected tachyarrhythmia is classified as AT. The detection of cardiac event patterns including the SVT pattern is discussed in U.S. patent application Ser. No. 11/276,213, entitled "RHYTHM DISCRIMINATION OF SUDDEN ONSET AND ONE-TO-ONE TACHYARRHYTHMIA", filed on Feb. 17, 2006, assigned to Cardiac Pacemakers, Inc., which is hereby incorporated in its entirety. If these conditions are not met at 1020, the detected tachyarrhythmia is classified as VT. AT is a pathologic tachyarrhythmia that occurs when a biologic pacemaker (focus) in an atrium usurps control of the heart rate from the SA node. In one embodiment, the third marginal correlation threshold ($FCC_{MTH3}$) is programmable between 0.4 and the correlation threshold (i.e., $0.4 \leq FCC_{MTH3} \leq FCC_{TH}$), with approximately 0.6 being a specific example. In one embodiment, the third marginal correlation threshold is set to be lower than the correlation threshold by a predetermined amount, such as approximately 0.4 (i.e., $FCC_{MTH3} \approx FCC_{TH} - 0.2$).

Figure 11:
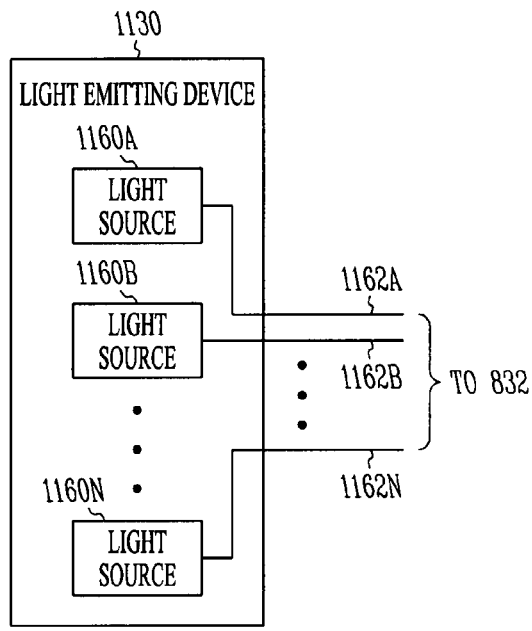
FIG. 11 is a block diagram illustrating an embodiment of a light emitting device of the optical anti-tachycardia system.

FIG. 11 is a block diagram illustrating an embodiment of a light emitting device 1130, which is a specific embodiment of light emitting device 830. In the illustrated embodiment, light emitting device 1130 includes light sources 1160A-N connected to control circuit 832 via electrical conductors 1162A-N, which extend within a lead coupling light emitting device 1130 to implantable medical device 701, such as lead 110 or 120. In various embodiments, light sources 1160A-N represent one or more light sources, and electrical conductors 1162A-N represent the corresponding the electrical conductors providing each of the one or more light sources with electrical connection to control circuit 832. In one embodiment, use of multiple electrical conductors to control multiple light sources allows individual control of each of the light sources.

Light sources 1160A-N are configured to deliver a light having specified frequency characteristics. In one embodiment, light sources 1160A-N include light emitting diodes (LEDs) each configured to deliver the light. In another embodiment, light sources 1160A-N include laser generators each configured to deliver the light in the form of laser. In another embodiment, light sources 1160A-N each include a broad spectrum light source and an optical filter configured to produce the light having the specified frequency characteristics.

In one embodiment, light sources 1160A-N (representing one or more light sources) are arranged to project the light to an identified tachyarrhythmia focus. In another embodiment, light sources 1160A-N (representing one or more light sources) are arranged to project the light to an identified cardiac region, such as a cardiac region having multiple tachyarrhythmia foci and/or a tachyarrhythmia reentrant loop. In a specific embodiment, light emitting device 1130 is configured for epicardial placement, such as light emitting device 716, and includes an epicardial patch on which light sources 1160A-N are incorporated.

Figure 12:
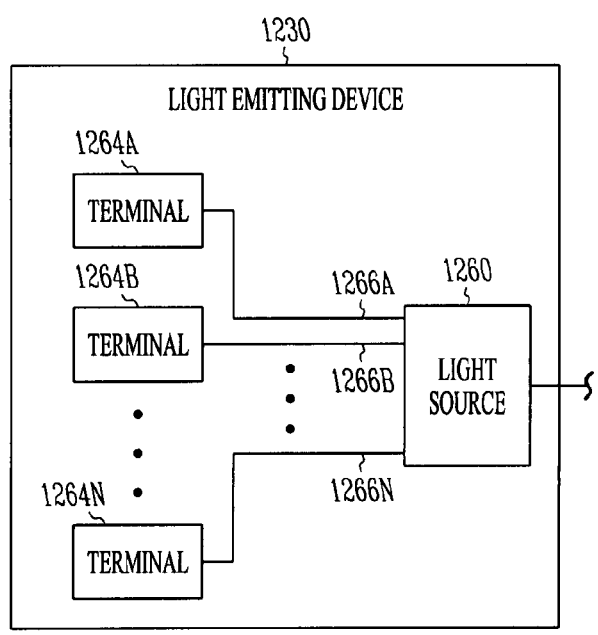
FIG. 12 is a block diagram illustrating another embodiment of a light emitting device of the optical anti-tachycardia system.

FIG. 12 is a block diagram illustrating another embodiment of a light emitting device 1230, which is another specific embodiment of light emission device 830. In the illustrated embodiment, light emitting device 1230 includes light emitting terminals 1264A-N connected to a light source 1260 via optical fibers 1266A-N, which extend within a lead coupling light emitting terminals 1264A-N to implantable medical device 701, such as lead 110 or 120. Light source 1260 is housed within implantable medical device 701. In various embodiments, light emitting terminals 1264A-N represent one or more light emitting terminals, and optical fibers 1266A-N represent the corresponding one or more optical fibers.

Light source 1260 is configured to deliver a light having specified frequency characteristics. In one embodiment, light source 1260 includes an LED configured to deliver the light. In another embodiment, light source 1260 includes a laser generator configured to deliver the light in the form of a laser. In another embodiment, light source 1260 includes a broad spectrum light source and an optical filter configured to produce the light having the specified frequency characteristics.

In one embodiment, light emitting terminals 1264A-N (representing one or more light emitting terminals) are arranged to project the light to an identified tachyarrhythmia focus. In another embodiment, light emitting terminals 1264A-N (representing one or more light emitting terminals) are arranged to project the light to an identified cardiac region, such as a cardiac region having multiple tachyarrhythmia foci and/or a tachyarrhythmia reentrant loop. In a specific embodiment, light emitting device 1230 is configured for epicardial placement, such as light emitting device 716, and includes an epicardial patch on which light emitting terminals 1264A-N are incorporated.

Figure 13:
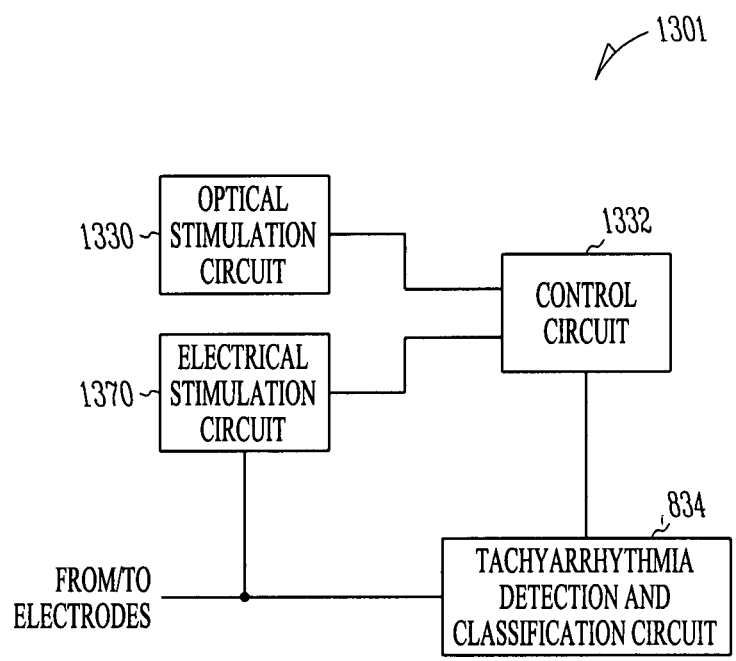
FIG. 13 is a block diagram illustrating an embodiment of an implantable medical device of the CRM system.

FIG. 13 is a block diagram illustrating an embodiment of an implantable medical device 1301, which is a specific embodiment of implantable medical device 701. Implantable medical device 1301 includes an ODS to deliver optical defibrillation therapy as well other optical and/or electrical stimulation therapies. In the illustrated embodiment, implantable medical device 1301 includes an optical stimulation circuit 1330, an electrical stimulation circuit 1370, a control circuit 1332, and tachyarrhythmia detection and classification circuit 834. Optical stimulation circuit 1330 delivers optical defibrillation and/or pacing therapies to heart 199. Electrical stimulation circuit 1370 delivers electrical defibrillation and/or pacing therapies to heart 199. Control circuit 1332 controls the delivery of each therapy as well as coordination of deliveries of different therapies. In one embodiment, implantable medical device 1301 provides for painless CRM therapies with electrical defibrillation as a back-up function. For example, in response to a detection of tachyarrhythmia by tachyarrhythmia detection and classification circuit 834, control circuit 1332 initiates an anti-tachyarrhythmia procedure including one or more attempts for terminating the detected tachyarrhythmia using one or more of electrical anti-tachycardia pacing (ATP), optical ATP, and optical defibrillation, depending on the classification of that tachyarrhythmia. If the detected tachyarrhythmia persists following the one or more attempts, electrical defibrillation is delivered.

In various embodiments, implantable medical device 1301 provides for optical stimulation for depolarizing cardiac tissue for pacing and/or defibrillation purposes in conjunction with other therapies such as electrical stimulation, drug delivery, and/or biologic therapy. In other embodiments, implantable medical device 1301 may also be used to provide for optical stimulation for depolarizing photosensitive tissue of any organ to regulate a function of that organ.

Figure 14:
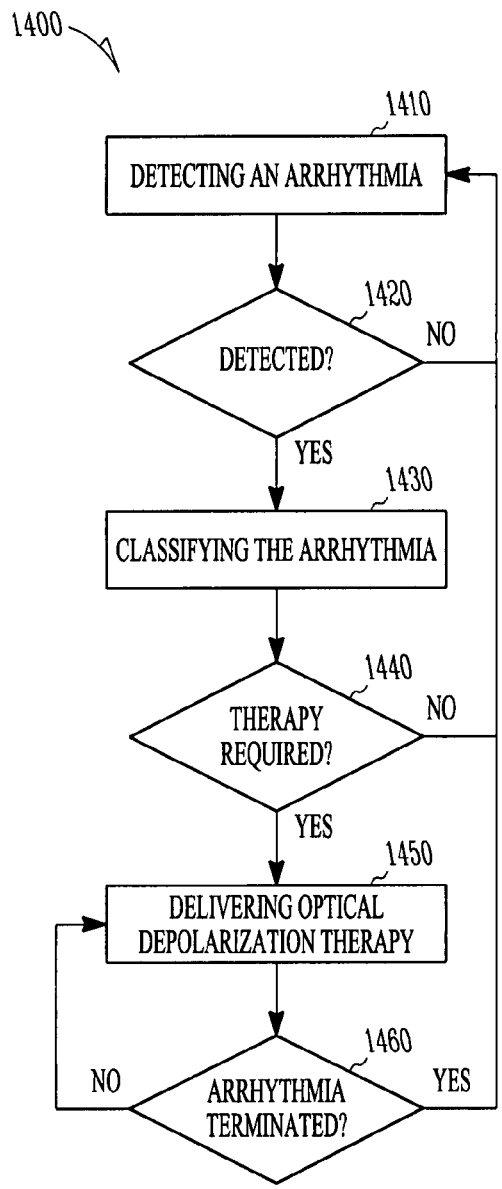
FIG. 14 is a flow chart illustrating an embodiment of a method for terminating arrhythmia using optical depolarization of cardiac tissue.

FIG. 14 is a flow chart illustrating an embodiment of a method 1400 for terminating arrhythmia using optical depolarization of cardiac tissue. The cardiac tissue is biologically treated to include photosensitive characteristics as discussed in this document. In one embodiment, method 1400 is performed using an ODS discussed in this document.

An arrhythmia is being detected at 1410 using a heart rate. If the arrhythmia is detected at 1420, it is classified at 1430. If the classification of the detected arrhythmia indicates that a therapy is required at 1440, an optical depolarization therapy is delivered at 1450. If the detected arrhythmia is not terminated at 1460, the optical depolarization therapy is repeated at 1450 until the detected arrhythmia is terminated, or until the optical depolarization therapy is determined not to be repeated based on predetermined criteria (because it is deemed to be ineffective, for example).

The optical depolarization therapy includes emission of a light having specified frequency characteristics suitable for optically depolarizing the cardiac tissue that is photosensitive. In one embodiment, the arrhythmia to be detected at 1410 includes tachyarrhythmia, and the detected tachyarrhythmia is classified at 1430 using a tachyarrhythmia classification method such as method 1000. The optical depolarization therapy includes an optical defibrillation therapy that delivers blue light or red light to a specified cardiac region using an endocardially or epicardially placed light emitting device. In one embodiment, the optical depolarization therapy includes an optical pacing therapy that delivers blue light or green light to a specified cardiac region using an endocardially or epicardially placed light emitting device.

Figure 15:
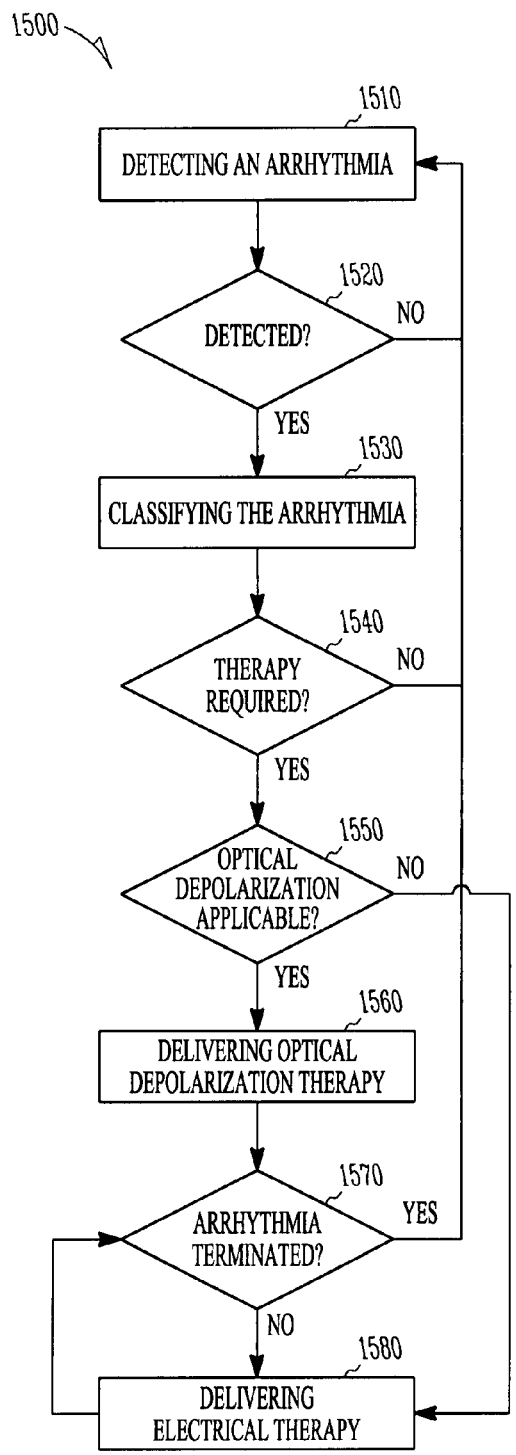
FIG. 15 is a flow chart illustrating another embodiment of a method for terminating arrhythmia using optical depolarization of cardiac tissue.

FIG. 15 is a flow chart illustrating an embodiment of a method 1500 for terminating arrhythmia using optical depolarization of cardiac tissue with electrical therapy as a backup. The cardiac tissue is treated so as to be photosensitive as discussed in this document. In one embodiment, method 1500 is performed using a CRM system including an ODS, as discussed in this document.

An arrhythmia is being detected at 1510 using a heart rate. If the arrhythmia is detected at 1520, it is classified at 1530. If the classification of the detected arrhythmia indicates that a therapy is required at 1540 and indicates that optical depolarization is applicable at 1550, an optical depolarization therapy is delivered at 1560. If the detected arrhythmia is not terminated at 1570, an electrical therapy, such as electrical pacing, cardioversion, or defibrillation therapy, is delivered at 1580 and repeated if necessary, until the detected arrhythmia is terminated. In one embodiment, if the detected arrhythmia is not terminated at 1570, the optical depolarization therapy is repeated for a specified number of attempts. The electrical therapy is delivered at 1580 after the optical depolarization therapy is deemed ineffective. If the classification of the detected arrhythmia indicates that a therapy is required at 1540 but indicates that optical depolarization is not applicable at 1550, the electrical therapy is delivered at 1580 and repeated if necessary, until the detected arrhythmia is terminated.

The optical depolarization therapy includes emission of a light having specified frequency characteristics suitable for optically depolarizing the cardiac tissue that is photosensitive. In one embodiment, the arrhythmia to be detected at 1510 includes tachyarrhythmia, and the detected tachyarrhythmia is classified at 1530 using a tachyarrhythmia classification method such as method 1000. The optical depolarization therapy includes an optical defibrillation therapy that delivers blue light or red light to a specified cardiac region using an endocardially or epicardially placed light emitting device. The electrical therapy includes a defibrillation therapy that includes delivery of one or more electrical defibrillation shocks as a backup therapy for the optical defibrillation therapy. In one embodiment, the optical depolarization therapy includes an optical pacing therapy that delivers blue light or red light to a specified cardiac region using an endocardially or epicardially placed light emitting device. The electrical therapy includes a pacing therapy that includes delivery of electrical pacing pulses as a backup therapy for the optical pacing therapy. In other embodiments, one or more other therapies, including electrical therapies other than the electrical pacing, cardioversion, and defibrillation therapy, are applied as the backup therapy for the optical depolarization therapy.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

---

What is claimed is:

1. A cardiac rhythm management system for stimulating a heart having photosensitive tissue, the system comprising:
a light emitting device configured to emit light having frequency characteristics suitable for depolarization of the photosensitive tissue;
a tachyarrhythmia detection and classification circuit adapted to detect tachyarrhythmia using a ventricular rate and a plurality of tachyarrhythmia rate zones each including a threshold rate and classify the detected tachyarrhythmia using one or more of an atrial rate, the ventricular rate, an onset rate of the detected tachyarrhythmia, a stability parameter indicative of a degree of variability of the ventricular rate, and a correlation coefficient representative of a correlation between a cardiac signal waveform sensed during the detected tachyarrhythmia and a template waveform; and
a control circuit coupled to the light emitting device and the tachyarrhythmia detection and classification circuit, the control circuit adapted to control the emission of the light for a period of time to depolarize the photosensitive tissue in response to the detected tachyarrhythmia being classified as a type to be terminated.

2. The system of claim 1 wherein the light emitting device is configured to emit a light having one or more wavelengths between 340 and 700 nanometers.

3. The system of claim 1 comprising an implantable lead, wherein the light emitting device comprises one or more light sources incorporated into the implantable lead.

4. The system of claim 3 wherein the one or more light sources comprise one or more light emitting diodes (LEDs).

5. The system of claim 1 comprising an implantable lead, wherein the light emitting device comprises:
one or more light emitting terminals on portions of the implantable lead;
a light source; and
one or more optical fibers extending within the implantable lead to connect the one or more light emitting terminals to the light source.

6. The system of claim 5 wherein the light source comprises a light emitting diode (LED).

7. The system of claim 1 comprising an electrical stimulation circuit coupled to the control circuit, the electrical stimulation circuit adapted to deliver one or more of electrical pacing pulses and electrical defibrillation shocks.

8. A method for treating an tachyarrhythmia, comprising:
detecting tachyarrhythmia using a ventricular rate and a plurality of tachyarrhythmia rate zones each including a threshold rate;
classifying the detected tachyarrhythmia using one or more of an atrial rate, the ventricular rate, an onset rate of the detected tachyarrhythmia, a stability parameter indicative of a degree of variability of the ventricular rate, and a correlation coefficient representative of a correlation between a cardiac signal waveform sensed during the detected tachyarrhythmia and a template waveform; and
emitting a light to a cardiac region including photosensitive tissue if the detected tachyarrhythmia is classified as a type suitable for therapy, the emitted light having frequency characteristics suitable for depolarizing the photosensitive tissue, wherein the light is emitted for a period of time to depolarize the photosensitive tissue.

9. The method of claim 8 further comprising delivering an electrical defibrillation shock if the detected tachyarrhythmia persists following the emission of the light.

10. The method of claim 8 further comprising delivering an electrical defibrillation shock if the detected arrhythmia is classified as a type not suitable for therapy.

11. The method of claim 8 wherein emitting the light comprises emitting a light having one or more wavelengths between 340 and 700 nanometers.

12. The method of claim 11 wherein emitting the light comprises emitting the light using multiple light sources.

13. The method of claim 12 comprising individually controlling each of the multiple light sources.

14. The method of claim 8 wherein the emitted light is selected to depolarize photosensitive tissue modified to include a light sensitive, variant ion channel protein or a light sensitive, variant protein that activates a G-protein signaling cascade that activates an ion channel, wherein the variant protein has one or more substitutions that shift the wavelength of light that the variant is sensitive to relative to a corresponding wild-type light sensitive protein.

15. The method of claim 14 wherein the variant is sensitive to blue light.

* * * * *